United States Patent [19]
Dau et al.

[11] Patent Number: 6,013,444
[45] Date of Patent: Jan. 11, 2000

[54] DNA BRACKETING LOCUS COMPATIBLE STANDARDS FOR ELECTROPHORESIS

[75] Inventors: Peter C. Dau, Winnetka; Debang Liu, Wilmette, both of Ill.

[73] Assignee: Oligotrail, LLC, Evanston, Ill.

[21] Appl. No.: 08/933,358

[22] Filed: Sep. 18, 1997

[51] Int. Cl.$^7$ .............................. C12Q 1/68; C12P 19/34; C07H 21/04
[52] U.S. Cl. ........................ 435/6; 435/91.2; 536/24.33
[58] Field of Search .............................. 435/6, 91.2, 810, 435/91.1; 536/24.33, 23.1, 25.3

[56] References Cited

U.S. PATENT DOCUMENTS

| | | | |
|---|---|---|---|
| 5,364,759 | 11/1994 | Caskey et al. | 435/6 |
| 5,599,666 | 2/1997 | Schumm et al. | 435/6 |

OTHER PUBLICATIONS

Schumm, J. W., "Gene Print ™ STR* Multiplexes: Reliability, Flexibility and Throughput in Database and Casework–Compatible STR Analysis," *Profiles in DNA*, 1997, pp. 9–13.

Liu, D, et al., "Intrafamily fragment analysis of the T cell receptor β chain CDR3 region," *Journal of Immunological Methods*, 1995, pp. 139–150.

Beckman, J.S. & Soller, M., "Toward a Unified Approach to Genetic Mapping of Eukaryotes Based on Sequence Tagged Microsatellite Sites," *Biochemistry*, vol. 8, 1990, pp. 930–932.

Peake, I.R., et al., "Family Studies and Prenatal Diagnosis in Severe von Willebrand Disease by Polymerase Chain Reaction Amplification of a Variable Number Tandem Repeat Region of the von Willebrand Factor Gene," *Blood*, vol. 76, No. 3, 1990, pp. 555–561.

Zuliani, G & Hobbs H., "A High Frequency of Length Polymorphisms in Repeated Sequences Adjacent to Alu Sequences," *American Journal of Human Genetics*, vol. 46, 1990, pp. 963–969.

Weber, J. L. & May, P.E., "Abundant Class of Human DNA Polymorphisms Which Can be Typed Using the Polymerase Chain Reaction," *American Journal of Human Genetics*, vol. 44, 1989, pp. 388–396.

"Molecular Applicants in Clinical Genetics," *American Journal of Human Genetics*, vol. 47, 1990, pp. A225 (0886) 2.7.

Tantz, R., "Hypervariability of simple sequences as a general source for polymorphic DNA markers," *Nucleic Acids Research*, vol. 17, No. 16, 1989, pp. 6463–6471.

D. Liu, et al., Intrafamily fragment analysis of the T cell receptor B chain CDR3 Region; Journal of Immunological Methods; vol. 187, 1995, pp. 139–150.

J. Schumm, Ph.D.; GenePrint STR* Multiplexes Reliability, Flexibility and Throughput in Database and Casework–Compatible STR Analysis; Geneprint Products; 1997; pp. 9–13.

Celi (1993) Nucleic Acids Research, vol. 21(4) p. 1042.

Candrian, et al (1992) Molecular & Cellular Probes, vol. 6 pp. 13–19.

*Primary Examiner*—Kenneth R. Horlick
*Attorney, Agent, or Firm*—Whitham, Curtis & Whitham

[57] ABSTRACT

The present invention is directed to an assay system, a kit, and a process for detecting the length of a polymorphic region of a genetic locus by means of bracketing locus compatible or specific calibrating DNA markers upon electrophoresis in a viscous medium.

57 Claims, 9 Drawing Sheets

F13A01--Extended Flanking Sequences

DNA BRACKETING LOCUS COMPATIBLE STANDARDS FOR ELECTROPHORESIS

BACKGROUND OF THE INVENTION

1. Field of the Invention

The invention is generally related to the measurement of the length of unknown deoxyribonucleic acid (DNA) fragments using an electrophoresis system and, more specifically, to the manufacture and use of bracketing pairs of DNA standards closely related in sequence and preferably derived from the DNA locus to be measured.

2. Definitions

U.S. Pat. No. 5,364,759 to Caskey et al. provides a concise definition for several terms used in biotechnology, particularly as they pertain to short tandem repeat polymorphisms. The complete contents of U.S. Pat. No. 5,364,759 is hereby incorporated by reference. The following definitions are provided to assist in providing a clear and consistent understanding of the invention.

Allele: a genetic variation associated with a segment of DNA, i.e., one of two or more alternate forms of a DNA sequence occupying the same polymorphic region of a genetic locus.

Allelic ladder: standard size marker consisting of amplified alleles from the polymorphic region.

Biochemical nomenclature: standard biochemical nomenclature is used herein in which the nucleotide bases are designated as adenine, A; thymine, T; guanine, G; and cytosine, C. Corresponding nucleotides are, for example, deoxyguanosine-5'triphosphate (dGTP), etc.

Deviation: the difference between the known (expected) length of a polymorphic DNA fragment and its measured length upon gel electrophoresis calibrated by coelectrophoresis of various DNA standard markers.

Differentially labeled: indicates that each extension product can be distinguished from all others because it has a different label attached and/or is of a different size and/or binds to a specifically labeled oligonucleotide. One of ordinary skill in the art will recognize that a variety of labels are available. Various factors affect the choice of the label. These include the effect of the label on the rate of hybridization and binding of the primer to the DNA, the sensitivity of the label, the ease of making the labeled primer, probe or extension products, the ability to automate, the available instrumentation, convenience, and the like.

Extension product: refers to the nucleotide sequence which is synthesized from the 3' end of the oligonucleotide primer and which is complementary to the strand to which the oligonucleotide primer is bound.

Flanking sequence: refers to the nucleotide sequence on either side of the part of the polymorphic region of the genetic locus to be amplified. "Unique flanking sequences" are those flanking sequences which are only found at one location within the genome.

Locus (or genetic locus): a specific position on a chromosome. Alleles of a locus are located at identical sites on homologous chromosomes.

Locus compatible marker: a DNA standard marker manufactured for use in gel electrophoretic determination of DNA fragment lengths of a polymorphic genetic locus from which it is derived through modification of the length of flanking sequence from a true or null allele of that locus. Locus compatible markers constitute part of the invention described herein.

Locus specific STR marker: a DNA standard marker manufactured for use in gel electrophoretic determination of DNA fragment lengths of a polymorphic genetic locus by subtracting or adding tandem repeat units to create novel alleles shorter than all known or common true alleles or longer than all known or common true alleles. Locus specific STR markers constitute another part of the invention described herein.

Locus specific primer: a primer that specifically hybridizes with a portion of a unique flanking sequence of a stated locus or its complementary strand, at least for one allele of the locus, and does not hybridize efficiently with other DNA sequences under the conditions used in the amplification method.

Multiplex polymerase chain reaction (mPCR): refers to a variation of PCR involving a procedure for simultaneously performing PCR on greater than two different sequences. In mPCR, after formation of two single stranded complimentary strands, a plurality of labeled paired oligonucleotide primers, where each pair is specific for a different sequence, are added. One primer of each pair is substantially complimentary for the part of the sequence in the sense strand and the other primer of each pair is substantially complimentary to a different part of the same sequence in the complementary antisense strand. The plurality of paired primers are annealed to their complementary sequence and simultaneously extended from each primer in each primer pair. The extension products then serve as a template for the other primer of each pair.

Polymorphism: refers to the genetic variation found in part of the genetic locus to be amplified.

Polymerase Chain Reaction (PCR): a technique in which cycles of denaturation, annealing with primer, and extension with DNA polymerase, are used to amplify the number of copies of a target DNA sequence by $>10^6$ times. The PCR process is described more fully in U.S. Pat. No. 4,683,195 and U.S. Pat. No. 4,683,202, both of which are herein incorporated by reference.

Primers: two single-stranded oligonucleotides or DNA fragments which hybridize opposing strands of a locus such that the 3' termini of the primers are in closest proximity.

Primer pair: a set of primers including a 5' forward primer that hybridizes with the 5' end of the DNA sequence to be amplified and a 3' reverse primer which hybridizes with the complement of the 3' end of the sequence to be amplified.

Primer site: the area of the target DNA to which a primer hybridizes.

Run time: the time required for a DNA fragment to migrate in an electric field through a fixed length of gel or other matrix and reach a detector.

Variant allele: a manufactured STR allele of a genetic locus incorporating repeat unit(s) or core repeat unit(s) of its polymorphism and either shorter or longer than all alleles or common alleles of its locus due to its variant number of repeat units. Variant alleles constitute part of the invention described herein.

DESCRIPTION OF THE PRIOR ART

Classical approaches to electrophoretic size determination compare unknown sample DNA fragments to DNA fragments of completely different sequences but known length. Sizing standards are generally prepared by restriction digestion of plasmid or bacteriophage DNA or by PCR amplification of well characterized templates. While powerful in application, these approaches suffer from the phenomenon that different DNA sequences may produce distinct DNA conformation dynamics resulting in different mobilities of fragments of identical length. Thus, standards and sample DNA fragments of identical length may appear as different sizes in gel electrophoresis.

The electrophoretic mobility of denatured DNA is primarily a function of fragment length. However, several factors affect mobility including the type of electrophoretic medium (solution vs. gel), type, concentration, polymerization and cross-linking of retarding molecules, buffers, electric field strength, and temperature. Because of the inherently variable mobility of DNA under different running conditions, as well as lane to lane and run to run variability under the same apparent running conditions, standard DNA fragments of known length are co-electrophoresed as part of each run in order to provide reference calibration of the sample DNA of unknown length.

For some purposes, simple visual comparison of stained sample bands after electrophoresis with co-electrophoresed standard fragments may be adequate to identify unknown samples. The advent of automated DNA sequencers has now made possible the resolution of DNA fragments different by as little as one nucleotide (1 nt), and these instruments can employ both external and internal DNA standards simultaneously to generate calibration curves and automatically read sample fragment lengths.

The local Southern calibration formula, or related formulae, are commonly employed to convert electrophoretic mobility to fragment length (see, Elder and Southern, "Computer-aided analysis of one-dimensional restriction fragment gels", Bishop, M. J., Rawlings, C. J. (Eds.), *Nucleic Acid and Protein Sequence Analysis*, IRL Press, Oxford, 1987). It uses the local segment of the calibration curve, as defined by the nearest neighboring standard markers which bracket the unknown sample, to generate a more accurate measurement than that found from the entire curve. Elder and Southern also reported that sequence related DNA provided more accurate calibration than DNA of heterologous sequence.

U.S. Pat. No. 5,599,666 to Schumm et al. discusses allelic ladders in general and, allelic ladders for short tandem repeat (STR) loci in particular, and the complete contents of this patent are herein incorporated by reference. As explained in Schumm, early work with allelic ladders involved mixing of amplified alleles from several individuals (i.e., independent genomic DNA samples) and subjecting them to electrophoretic separation. The separated alleles were labeled by inclusion of a fluorescent primer which is identified using a fluorescence detector. In Schumm, a STR sequence from DNA at a specific locus is identified using STR allelic ladders containing nucleotide fragments of the same length as two or more known alleles for the locus. Furthermore, in Schumm, the allelic ladder components are characterized by sequence analysis. Fragments composing the allelic ladder are identical in size and sequence to the amplified alleles to be identified from sample material, and therefore have the same size and sequence dependent electrophoretic mobility as the fragments to be analyzed regardless of the gel system used for electrophoretic separation.

The T cell receptor (TCR) plays a key role in the recognition of microbes by the immune system. The molecular basis for its ability to do so lies in loops formed by the polymorphic CDR3 regions of its alpha (A) and beta (B) chains, which directly contact antigenic fragments bound in a groove formed by major histocompatibility molecules. TCR genes play a central role not only in microbial immunity but in tumor immunity, autoimmunity, alloimmunity, and immunodeficiency. Therefore, the identification of TCR genes involved in these immune conditions is of vital importance.

TCR CDR3 regions are hypervariable in both sequence and length, and lie between the 5' variable, V, segments and the 3' constant, C, segments of TCR genes, and are formed by nucleotides from the diversity, D, and junctional, J, segments as well as N nucleotides in B chains and J segments and N nucleotides in A chains. There are over fifty (50) known A chain and forty-five (45) known B chain TCRV segment genes. They are grouped in 32 A chain families (see, Moss et al., *Eur. J. Immunol*.23:1153–1159 (1992)) and 25 B chain families or subfamilies (see, Rowen et al. *Science* 272:1755–1762, 1996) based upon sequence homology within there V gene segments.

When families of these genes from polyclonal T lymphocyte populations are amplified with PCR employing flanking primers hybridizing in the V and C segments to amplify TCR genes across their CDR3 regions, it is found that they yield a polymorphic series of CDR3 lengths from 0 to 60 nt (see, Liu et al., *J. Immun. Meth*., 187:139–150 (1995)). Upon electrophoresis on polyacrylamide sequencing gels under denaturing conditions, the different gene fragments are resolved as peaks differing by multiples of 3 nt, corresponding to a single amino acid difference in the CDR3 length. Consequently, in order to accurately relate isolated, cloned TCR A and B chain gene fragments back to their population of origin, the electrophoretic measurement error should be <1.5 nt. This goal is not generally obtainable with the heterologous DNA standards currently employed.

Precise electrophoretic identification of DNA fragment lengths is required for the measurement of polymorphic genetic loci containing STR sequences. STR loci contain tandemly repeated sequence elements of 2–7 base pairs (bp) in length, providing a rich source of stable, heritable, polymorphic markers resulting from variation in the numbers of copies of the repeated motif Tri- and tetrameric STRs occur as frequently as every 15 kilobases (kb) in the human genome, forming up to 200,000 individual loci (see Beckman and Weber, *Genomics*, 12:627–631 (1992)). STRs have proven useful in human identification, paternity testing and linkage analysis, and are preferred for these applications because of their ease of use and reproducibility. Sheffield et al., *Hum. Mol. Gen*. 4:1837–1844, 1991, for example, have described the use of over 2,000 of these loci in constructing genome-wide human linkage maps. Minisatellite loci with large repeat units and STR loci with 2 bp repeat units manifest properties similar to other STR loci, but for technical reasons are more difficult to analyze. Some STR loci, especially those containing tetranucleotide repeats, may exhibit non-integer alleles differing in size by only 1 or 2 nt (see, Puers et al., *Science*, 272:1755–1762 (1993)). Since allelic designations are rounded to the nearest nt, an error of less than 0.5 nt is therefore desirable for STR allele detection.

STR polymorphisms are amplified from genomic DNA by PCR employing specific primer sequences hybridizing with their 5' and 3' flanking sequences in a manner analogous to employing flanking V and C segment specific primers of TCR genes to amplify their polymorphic CDR3 regions. Primer pairs for different STR loci, usually 4 to 8, are often combined together in multiplex PCR.

Allelic forms of an STR locus are differentiated by the number of copies of the repeat sequence contained within the amplified region, as determined by their fragment lengths upon electrophoresis, and are numbered according to the number of repeat units. Identification of allelic PCR fragments has generally been carried out electrophoretically on slab gels employing heterologous DNA fragment markers as calibrating standards in internal lanes or both internally and externally (internal standards being performed by running a standard in the same lane as the sample; external standards being performed by running a standard in a lane adjacent to the sample lane). Standards for capillary electrophoresis are often run on the same gel, but on a different run, either before or after the unknown sample. More reliable standards composed of non-locus specific DNA are concatamers of 20 to 50 mer units which vary in length by one unit have been recently developed (see, Vanier et al., Genomics 41:1–9, 1997). These homopolymers show minimal differences among themselves in sequence derived electrophoretic mobility.

Of the external lane markers, the most reliable ladders are compounded from the alleles themselves (see, Sprecher et al., BioTechniques 20:266–277, 1996), with which they share the sequence of the DNA sample allelic fragments to be measured. However, allelic ladders are difficult to employ as internal lane standards because they migrate in the same positions on the gel as the unknown DNA fragments, thereby obscuring their detection. In spite of this problem, Moscetti et al., Electrophoresis 16:1875–1880, 1995, used sample peak signal enhancement by overlapping alleles labeled with the same fluorophore as the unknown sample as a method of detection. Smith, BioTechniques 18:122–128, 1995, employed three different fluorophores within a single STR locus to demonstrate that in lane allelic ladders were superior to heterologous DNA standards. Energy transfer fluorophores have been developed for use with allelic and non-locus specific standards and unknown samples. They are excited by a common laser, but produce non-overlapping detectable emissions (see Wang et al., Anal. Chem. 67:1197–1203, 1995; Wang et al., Electrophoresis 17:1485–1490, 1996).

SUMMARY OF THE INVENTION

It is an object of this invention to provide a method of producing bracketing, locus compatible, or specific DNA standards of known length and sequence which can be used in a variety of applications including, in particular, the measurement of TCR A and TCR B gene polymorphic CDR3 regions.

It is another object of this invention to provide a method of producing DNA standards derived from the locus to be measured which are coelectrophoresed with polymorphic DNA samples, either internally or externally, as bracketing, locus compatible, or specific DNA standards.

It is yet another object of this invention to provide a method of making and using locus specific STR markers for determining DNA fragment lengths.

According to the invention, sequence compatible or specific DNA markers for fragment length polymorphisms of a genetic locus are constructed with the goal of closely bracketing without overlap, the length of several or all known alleles of that locus upon electrophoretic separation. Because of their close sequence and fragment length relationship to the alleles of their targeted genetic locus, bracketing locus compatible markers co-electrophoresed in the same lane as sample alleles from that locus provide precise calibrating standards for sample fragment length determination. It is another goal of this invention to provide PCR template fragment pairs for bracketing locus specific standards of sufficient length in their flanking sequences. These template pairs can be co-amplified together with the genomic sample DNA by the PCR primers employed for that locus. Co-amplification produces a positive control for the PCR reaction, as well bracketing internal standards for that locus. Co-amplification also provides an equal opportunity for bracketing markers and sample DNA having an extra nucleotide added to its 3' end by Taq DNA polymerase.

Furthermore, in another aspect of the invention, locus specific STR markers of a polymorphic genetic locus are created by either adding or subtracting tandem repeat units to create novel alleles which are either longer or shorter, respectively, than all known or common true alleles. These locus specific STR markers can be used in electrophoresis to determine DNA fragment lengths for the polymorphic genetic locus.

BRIEF DESCRIPTION OF THE DRAWINGS

The foregoing and other objects, aspects and advantages will be better understood from the following detailed description of the preferred embodiments of the invention with reference to the drawings, in which:

FIG. 10 is a photograph of a scan of an agarose gel electrophoresis showing DNA calibrating standard markers in lane 1; extended flanking regions amplified from the F13A01 locus of genomic DNA by reverse primer F13A01 rev 251-Eam-1 combined with forward primer F13A01 fwd from the 5' flanking sequence (lane 2) and by forward primer F13A01 fwd 248 Eam-2 combined with reverse primer F13A01 rev 628 from the 3' flanking sequence (lane 3); and lane 4 amplification of the 275 bp short F13A01 variant allele by the classical F13A01 locus specific primer pair from their ligation product (lanes 2+3).

DETAILED DESCRIPTION OF THE PREFERRED EMBODIMENTS OF THE INVENTION

Figure 1:
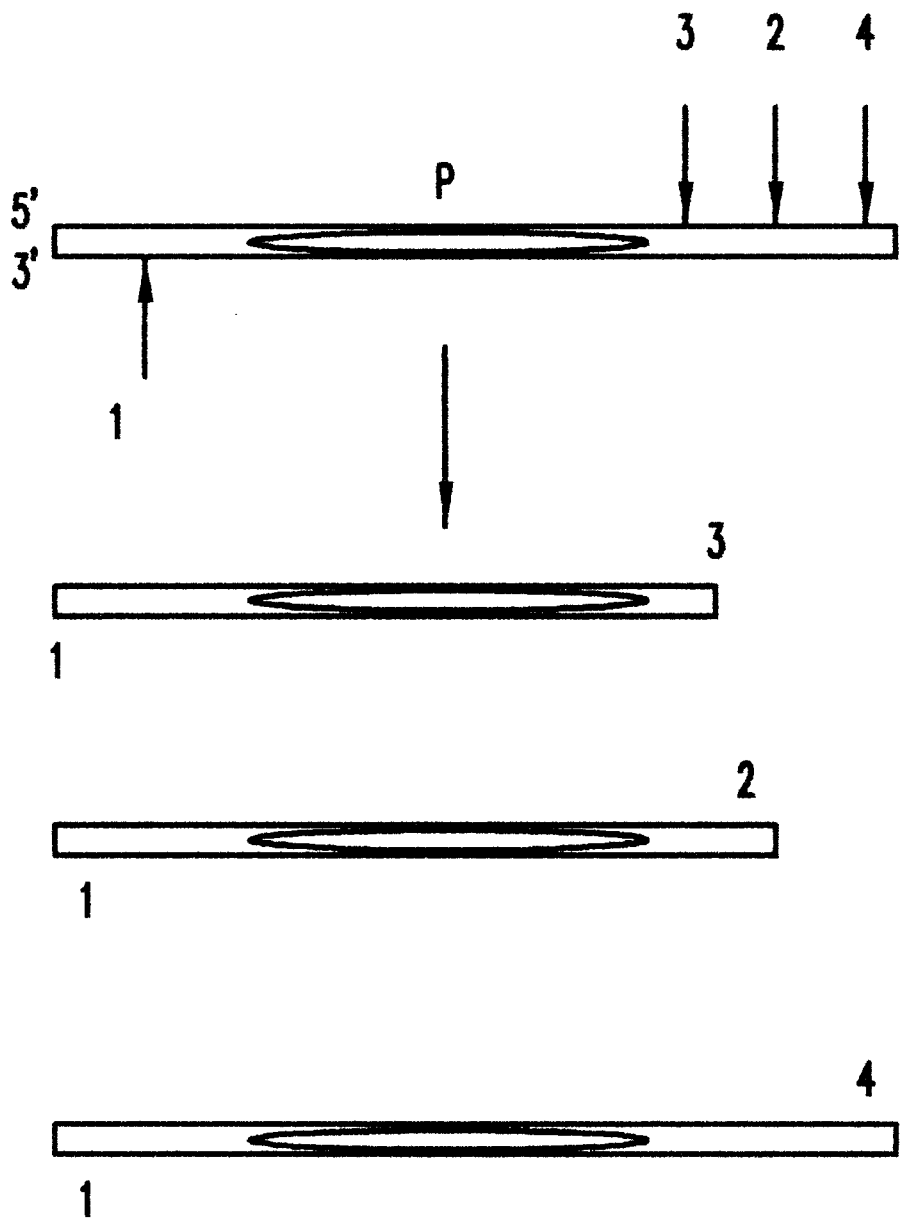
FIG. 1 is a schematic drawing showing one strategy used in the practice of this invention.

The system of the present invention provides a rapid, non-isotopic method which can be used to evaluate very small amounts (e.g., 1 ng) of human DNA. The preferred process includes the use of fluorescence emission to detect the presence of fluorophore labeled, amplified, locus compatible, length polymorphic DNA products upon separation by denaturing medium electrophoresis. It is also possible to detect these DNA fragments using radioactivity and various dyes or stains with denaturing or native DNA electrophoresis using any available gel or viscous matrix or other size separation methods.

Sequence compatible DNA markers for fragment length polymorphisms of a genetic locus are constructed with the goal of closely bracketing without overlapping the length of several or all known alleles of that locus upon electrophoretic separation. Because of their close sequence and fragment length relationship to the alleles of their targeted genetic locus, bracketing locus compatible markers co-electrophoresed in the same lane as sample alleles from that locus provide precise calibrating standards for sample fragment length determination.

The creation of locus compatible closely bracketing markers involves several introductory steps including obtaining DNA samples, cloning and sequencing, amplification, separation and detection. Based on these steps, locus compatible bracketing markers can be created. Each of the introductory steps is discussed below.

Obtaining DNA Samples-Several individuals are selected for DNA isolation. DNA is directly extracted from the blood, tissue, or tissue culture cells using standard methods (Puregene, Genta Systems, Minneapolis, Minn.). DNA concentration is determined by spectrophotometry. K562 control DNA is from Promega (Madison, Wis.).

RNA is extracted from $2-3 \times 10^6$ peripheral blood mononuclear cells (PBMC) obtained by density sedimentation (LSM, Organon Teknika, Durham, N.C.) of 10 ml of whole blood or human lymphocyte clones grown in our laboratory (RNAzol B, Tel-Test, Friendswood, Tex.). RNA concentration can be determined by the same instrument as DNA. First strand cDNA (33 µl) was synthesized from 1.0 µg total RNA using the first strand cDNA kit (Pharmacia, Piscataway, N.J.).

Cloning and Sequencing-T cell clones are established from PBMC by primary culture in microtiter wells under limiting dilution conditions (0.7 cell-well) in the presence of PHA, IL-2, and $10^5$ autologous irradiated (5000 rads) PBMC as feeder cells. Molecular cloning of blunt ended TCR PCR products was carried out with the PCR-Script Amp SK(+) cloning kit (Stratagene, La Jolla, Calif.). Cycle sequencing of clonal TCR fragments was carried out with fmol® DNA Cycle Sequencing System (Promega) and the A.L.F. automated DNA sequencer (Pharmacia).

Amplification-DNA samples are subjected to PCR amplification using primers and thermocycling conditions specific for each locus. Table 1 provides the sequence of locus specific primer pairs.

TABLE 1

Sequences and Location of Oligonucleotides

| Primer name | Seq. Id. No. | Primer seq. (5' ---> 3') | Position | Reference |
|---|---|---|---|---|
| TCRAV 7 | 1 | gcaacatgctgg cggagcacccac | 159–136 | Genevee, C. (1992) |
| TCRAC 27-Cy5[1] | 2 | cacggcagggtc agggttctg | 27–7 | Liu et al. |
| TCRAC 57-Cy5/F[2] | 3 | gtcactggatttag agtct | 57–39 | Genevee, C. (1992) |
| TCRAC 87-Cy5[1] | 4 | atcaaaatcggtg aataggcag | 87–66 | Liu et al. |
| TCRAC 129 | 5 | atacacatcagaa tccttactttg | 129–106 | Genevee, C (1992) |
| TCRBV 16 | 6 | aaagagtctaaa caggatgagtcc | 103–108 | Choi, Y. (1989) |
| TCRBC 24-Cy5/F[2] | 7 | tgggaacacgtttt tcag | 24–7 | Liu et al. |
| TCRBC 54-Cy5/F[2] | 8 | ttctgatggctcaa acac | 54–37 | Choi, Y. (1989) |
| TCRBC 78-Cy5[1] | 9 | cttttgggtgtggg agatctc | 78–58 | Liu et al. |
| TCRBC 92-Cy5/F[2] | 10 | cacaccagtgtg gccttttg | 92–73 | Liu et al. |
| TCRBC 168 | 11 | [4]tcgtcgacccca ctgtgcacctcctt ccc | 168–145 | Robinson, M. (1991) |
| [a]CSF1PO fwd 11848-F[3] | 12 | aacctgagtctgc caaggactagc | 11848–1187 | Hammond, H. (1994) |
| CSF1PO rev 12158 | 13 | acacaccactgg ccatcttc | 12158–12139 | Liu et al. |
| CSF1PO rev 12162-atct | 14 | [4]atctttccacaca ccactggccatct tc | 12162–12139 | Liu et al. |
| [b]F13A01 fwd 1 | 15 | aatcccaaca ctttgggaagc | 1–21 | Liu et al. |
| F13A01 fwd 190-Cy5/F[2] | 16 | gaggttgcactcc agcctttgcaa | 190–213 | Puers, C (1994) |
| F13A01 fwd 268-Eam-2 | 17 | atctcttcaaaga aagagtaaaga aaaaatt | 268–282 | Liu et al. |
| F13A01 fwd 248-Eam-9 | 18 | atctcttcaaaga aag(aaag)$_7$agt | 248–278 | Liu et al. |
| F13A01 rev 251-Eam-1 | 19 | atctcttcactttca tctttctatctttca gatg | 251–227 | Liu et al. |
| F13A01 rev 275-Eam-9 | 20 | atctcttcactttct tt(cttt)$_7$cat | 275–245 | Liu et al. |
| F13A01 rev 480 | 21 | tgaatcatcccag agccaca | 480–461 | Liu et al. |
| F13A01 rev 484 | 22 | ttcctgaatcatcc cagagccaca | 484–461 | Puers, C. (1994) |
| F13A01 rev 484-cttt | 23 | [4]cttttcctgaatc atcccagagcca ca | 484–461 | Liu et al. |
| F13A01 rev 488 | 24 | tgcattcctgaatc atcccagagcca ca | 488–461 | Liu et al. |
| F13A01 rev 628 | 25 | atgcttttgcctggc aggtcagc | 628–606 | Liu et al. |
| [c]FESFPS fwd 4649-F[3] | 26 | gcttgttaattcat gtagggaaggc | 4649–4673 | Hammond, H. (1994) |
| FESFPS rev 4884 | 27 | tcccagctacttg gctactc | 4884–4864 | Liu et al. |
| FESFPS rev 4888-attt | 28 | [4]atttgtagtccca gctacttggctact c | 488–4864 | Liu et al. |

[1]5' end of primer tagged with Cy5.
[2]5' end of primer is tagged with either Cy5 or fluorescein.
[3]5' end of primer is tagged with fluorescein.
[4]the underlined nucleotides are not complimentary to the genomic sequence.
[a]sequence reference: human c-fms proto-oncogene for CSF-1 receptor genebank accession X14720NID
[b]sequence reference: human coagulation factor XIII a subunit gene, 5' flank. Genebank accession M21986 J03834 NID g 182293.
[c]sequence reference: human c-fes/fps proto-oncogene. Genebank accession X06292M14209M14589NID.

References:

Liu et al.—Data presented herein

Genevee, C., *Eur. J. Immun.* 22:1261–1269 (1992)

Choi, Y., *Proc. Natl. Acad. Sci.* 86:8941–8945 (1989)

Robinson, M., *J. Immunol.* 146(12):4392–4397 (1991)

Hammond, H., *J. Hum. Genet.*, 55:175–189 (1994)

Puers, C., *Genomics* 23:260–264 (1994)

The examples below provide details on the specific procedure relating to each locus. The locus-specific primers include a number of nucleotides which, under the conditions used in the hybridization, are sufficient to hybridize with an allele of the locus to be amplified and to be essentially free from hybridization with alleles of other loci. Oligonucleotide primers were supplied by Operon Technologies (Alameda, Calif.). U.S. Pat. No. 5,192,659 to Simons more fully describes locus specific primers and that patent is herein incorporated by reference.

In one embodiment of this invention, the TCR A and B gene CDR3 polymorphisms were chosen for DNA fragment length determination. PCR primers hybridizing with family specific regions of the 5' flanking variable (VA) or (VB) segments served as forward primers, and primers hybridizing with the 3' flanking constant (CA) or (CB) segments served as the reverse primers (see, e.g., Liu et al., *J. Immuno. Meth.* 187:139–150, 1995). Each PCR reaction consisted of 1.0 $\mu$l forward and reverse primers, (3 $\mu$M each), 0.15 $\mu$l Taq DNA polymerase, 0.15 $\mu$l 10 $\mu$M dNTPs, 1.0 $\mu$l cDNA, and water to bring the final volume to 10.0 $\mu$l. PCR of 30 cycles was performed with denaturation at 94° C. for 45s, annealing at 55° C. for 45s, extension at 72° C. for 45s, and extension for 10 min at 72° C. after the last cycle.

In another embodiment 3 STR kits containing fluorescein labeled allelic ladders and primers from three individual loci were purchased from Promega (Gene Print Fluorescent STR systems, Promega, Madison, Wis.): CSF1PO, FESFPS, and F13A01. Taq DNA polymerase and 10× buffer were purchased from Boehringer Mannheim (Indianapolis, Ind.). A Perkin-Elmer 480 DNA thermocycler was used for PCR amplification using the Promega protocol 8 in their February, 1996 technical manual. STR sample DNA was amplified with STR locus specific primers (Promega) which hybridized to locus specific flanking sequences 5' and 3' to the tandem repeat region (Table 1). A DNA standard ladder with intervals from 50 through 500 bp was purchased from Pharmacia.

Separation and Detection of DNA Fragments

Amplification products are separated by electrophoresis, for example, by denaturing polyacrylamide gel electrophoresis. Electrophoresis is carried out in 0.5 mm thick 6% denaturing polyacrylamide pre-mixed gels and TBE Buffer (Gel-Mix 6 and Gel-Mix Running Mate, GIBCOBRL, Gaithersburg, Md.) on the automated DNA sequencers A.L.F. and A.L.F. Express (Pharmacia). Based on the manufacturers recommendations, the operating conditions for A.L.F./A.L.F. Express are voltage: 1500 V/1500 V; current: 38 mA/60 mA; power; 3 mW/3 mW, temperature: 42° C./55° C.

One member of each PCR primer pair is labeled with the appropriate fluorophore (fluorescein for the A.L.F., Cy5 for the A.L.F. Express) in order to tag one strand of all DNA fragments to be analyzed. The data is analyzed with Fragment Manager™ 1.2 software (Pharmacia) using the following settings: peak width 10, peak height 0.5, and cluster sensitivity 0. The software automatically determines fragment length based on sample electrophoretic mobility in the gel by comparison with known size markers in the same (internal markers) and/or different lanes (external markers). The amount of PCR product loaded on each gel lane is adjusted so that each fragment forms a single peak distinguishable from neighboring peaks.

Creation of Locus Compatible Bracketing Markers

The creation of locus compatible bracketing markers involves the use of PCR primers specific for unique flanking sequences of the polymorphic region of a genetic locus targeted for amplification. In the preferred embodiment, the primer is a single-stranded oligodeoxyribonucleotide of sufficient length to prime the synthesis of an extension product from a specific sequence in the presence of an inducing agent. Sensitivity and specificity of the oligonucleotide primers are determined by the primer length and uniqueness of sequence with a given sample of template DNA. In the present invention, the oligonucleotide primers are usually greater than 15 mer and in the preferred embodiment are about 20–30 mer or more in length.

Each pair of primers is selected to detect part of a different genetic locus. Each primer of each pair herein is selected to be substantially complementary to a different strand in the flanking sequence of each specific genetic sequence to be amplified. Thus, one primer of each pair is sufficiently complementary to hybridize with a part of the sequence in the sense strand and the other primer of each pair is sufficiently complimentary to hybridize with a different part of the same sequence in the antisense strand. Although the primer sequence need not reflect the exact sequence of the template, the more closely the 3' end reflects the exact sequence, the better the binding during the annealing stage.

In one embodiment, primers are directed to flanking sequence sites 5' and 3' to a classical site to produce amplification products shorter and longer than the classical product when combined with the other classical flanking sequence primer in a PCR reaction. The new amplification products would then migrate faster and slower than the classical product in an electrophoretic field, thereby serving as bracketing markers for the location of the classical product.

In another embodiment, newly designed primers may bind at sites partly congruent with a classical primer pair used to amplify a given polymorphic region, and different from them only by being shorter or longer. Short primers would be shortened on the end most distant from the targeted polymorphic locus so as to produce a shorter amplification product. Long primers would be lengthened on the end farthest away from the target locus so as to produce a lengthened amplification product. If paired with the classical locus specific primer from the opposite unique flanking sequence, they would then amplify shorter or longer DNA fragments, respectively, which would then bracket the conventionally amplified product upon electrophoretic fragment length analysis.

In a preferred embodiment, such modified locus specific primers are used to create standard electrophoretic markers by amplifying selected alleles of a desired length from a polymorphic region. A shortened primer is used to shorten a shortest allele or short infrequent allele from a polymorphic region of a genetic locus to create a short bracketing marker with electrophoretic mobility greater than any allele or any common allele of that polymorphic region. A lengthened primer is used to amplify the longest allele or a long infrequent allele from a polymorphic region of a genetic locus to create a long bracketing marker with electrophoretic mobility less than any allele or any common allele of that polymorphic region.

In another embodiment, sets of primer pairs are designed to alter the polymorphic region itself rather than its unique flanking sequences in order to create variant alleles shorter or longer than any naturally occurring allele or common allele. In this application, the same flanking sequence specific primers classically employed to amplify a polymorphic region are used to amplify variant alleles to produce pairs of closely bracketing amplification products with lesser or greater electrophoretic migration, respectively, than any alleles or common alleles of that polymorphic locus. Thus, the bracketing variant alleles can be amplified in the same PCR reaction as the sample alleles under analysis.

FIG. 1 schematically shows one embodiment of the invention wherein a deoxyribonucleic acid (DNA) fragment from a genetic locus of interest, conventionally having its sense strand identified as beginning with a 5' terminus and its antisense strand identified as ending with 3' terminus. It's polymorphic region "P" is amplified in PCR by a forward primer 1 and a reverse primer 2 which hybridize to its flanking sequences. Primers 3 and 4 are designed to hybridize with the same sense strand as reverse primer 2 at locations 5' and 3' from primer 2, respectively. Primers 3 and 4 could equally well be designed to hybridize with the same antisense strand as primer 1 at comparable locations 5' and 3' from primer 1.

In the preferred embodiment, each of the reverse primers 2, 3 and 4 are labeled with a marker, such as a fluorophore, radiometric marker, or any other suitable agent which can be detected and identified. Alternatively, the forward primer 1 could be labeled, and primers 2, 3, and 4 could be unlabeled, or all primers could be labeled. In the embodiment shown in FIG. 1, primers 2, 3, and 4 are used to create extension products of varying length. Upon undergoing PCR, fragments beginning with primer 1 and terminating with primers 2, 3 and 4 are produced. These fragments can be separated using electrophoresis and the shorter and longer extension products made with reverse primers 3 and 4, respectively, will bracket extension products produced with reverse primer 2. Insofar as the bracketing extension products will have an identical sequence within the region shared with classical fragments having primer 1 and primer 2 at their 5' and 3' termini, they will have similar mobility in the electrophoresis medium (e.g., a gel). In addition, because the length of the bracketing extension products amplified from known templates with primers 3 and 4 will be precisely known from their sequence, the length of an allelic region in an unknown sample amplified with primers 1 and 2 will be readily determined using the bracketing extension products as length calibrating markers. Furthermore, because the primers 3 and 4 are chosen so as not to overlap the amplified polymorphic region, their bracketing extension products will be readily discerned.

Figure 2:
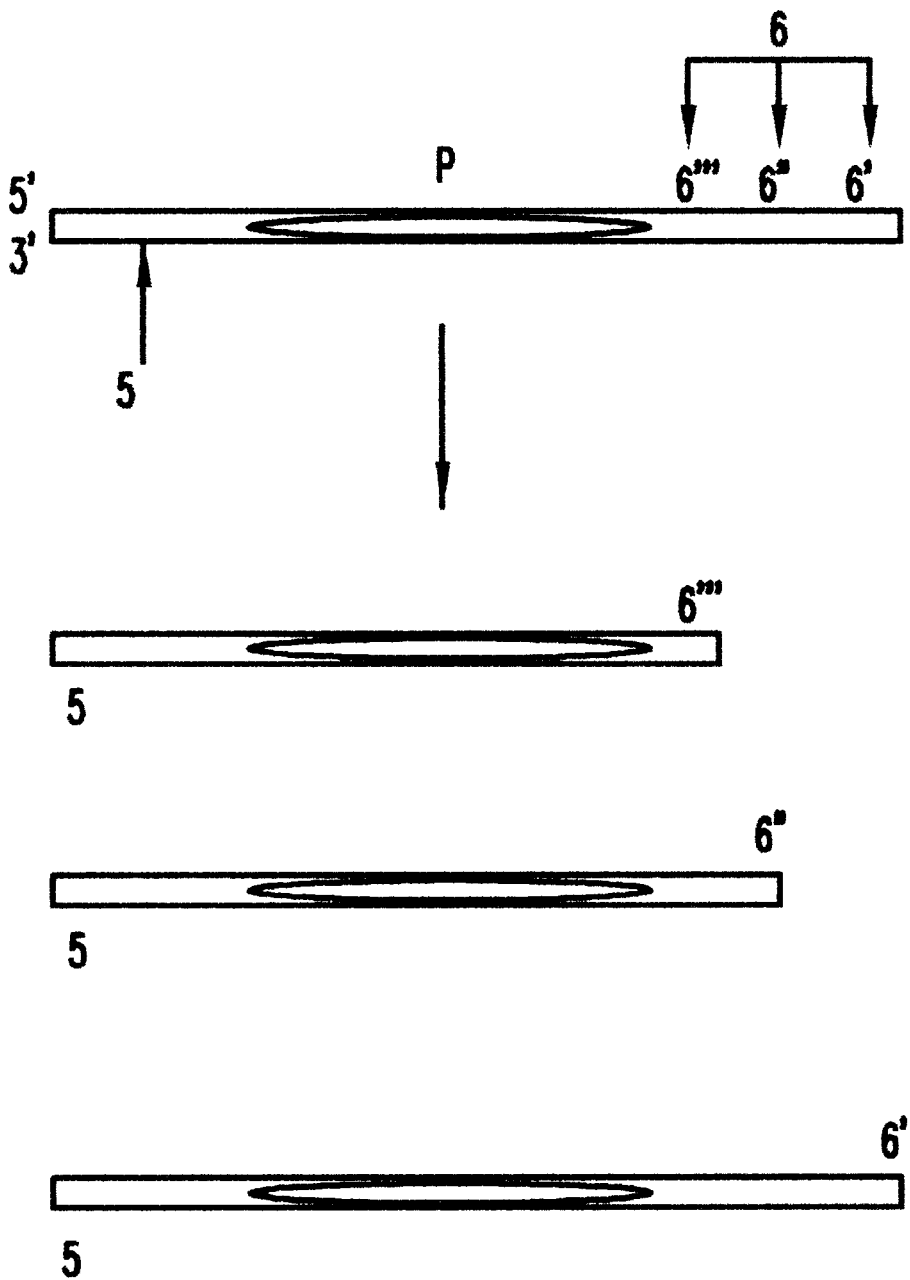
FIG. 2 is a schematic drawing showing another strategy used in the practice of this invention.

FIG. 2 shows a variation on the methodology shown in FIG. 1. Specifically, a polymorphic region of a genomic locus is bounded by a forward primer 5 on the antisense strand and reverse primers 6', 6", or 6'" on the sense strand. The reverse primer is preferably labeled with a fluorescent or radiometric label, and is selected from the nucleotide sequence 6. However, it should be understood that primer 5 could be labeled in the practice of this invention. The longest primer 6' constitutes all or most of the nucleotides in sequence 6. The primer 6" would preferably be a classical known primer for the genomic locus, and would be identical to the primer 6' except for an additional, known number of nucleotides present in 6'. The primer 6'" would be the shortest primer. Primer 6'" would have identical nucleotides to those found in the 5' end of primers 6", but would lack a few nucleotides at the 3' terminus.

Upon PCR, labeled fragments would be produced, each having primer 5 at the 5' end, and a labeled primer 6', 6", or 6'" at the 3' end. Upon electrophoresis, each of the fragments would have the same relative mobility because they have the same conformation, and the fragments terminating in 6' or 6'" would bracket the fragment terminating in 6". Because the number of nucleotides in the bracketed fragments are known, the length of an unknown fragment amplified with primer 6" will be readily determined with reference to known fragments amplified with primers 6' and 6'".

Figure 3:
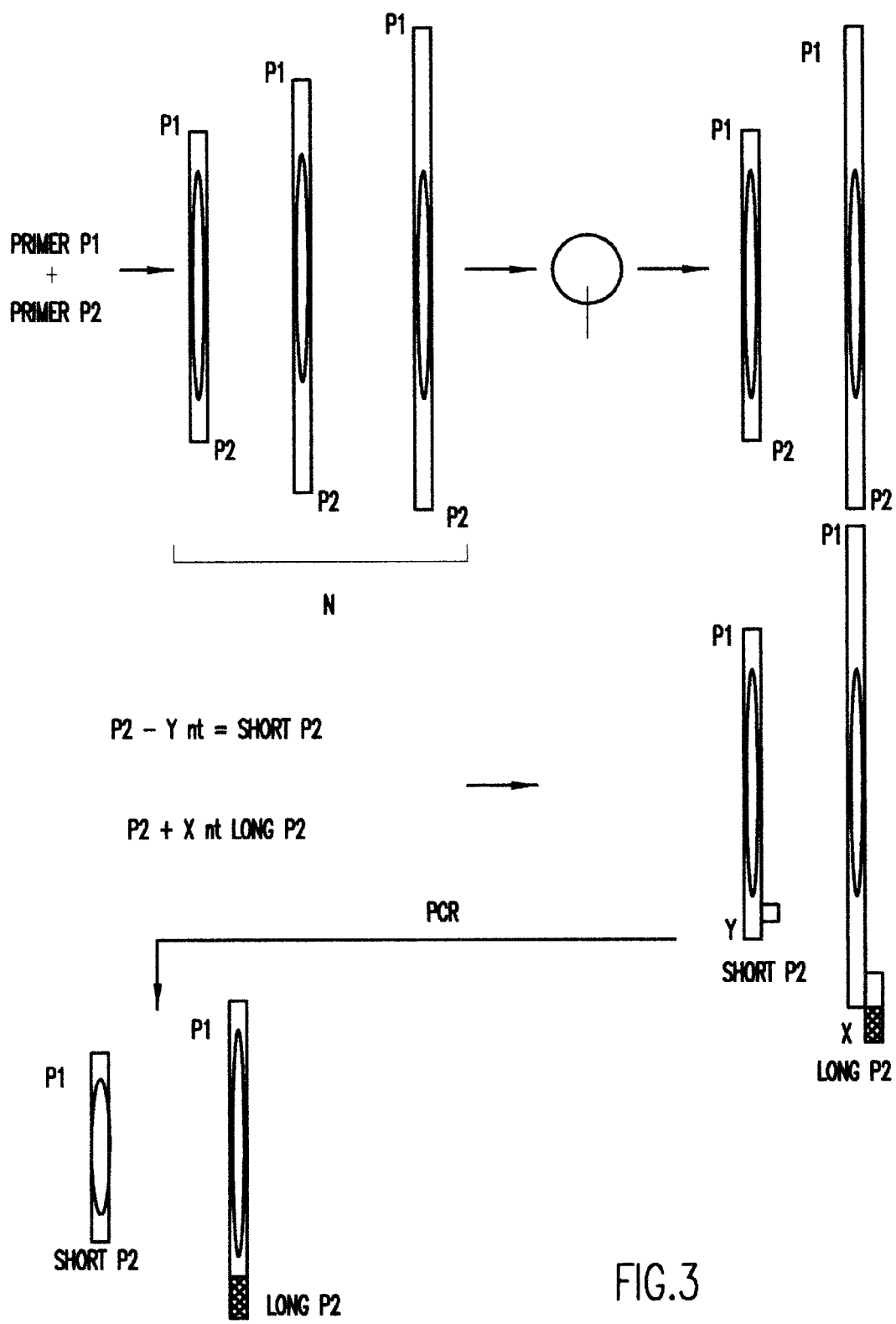
FIG. 3 is a schematic drawing showing another strategy used in the practice of this invention.

FIG. 3 shows an embodiment of this invention which is applicable to the creation of locus compatible bracketing markers for a short tandem repeat (STR) locus. An allelic ladder containing N alleles of different length is created from multiple samples of genomic DNA containing an STR locus using flanking sequence primers P1 and P2. The PCR amplified alleles are cloned into a plasmid vector, and transformed into bacteria. The shortest and longest alleles or common alleles are isolated. The alleles each terminate with nucleotide flanking sequences identical to primer P1 at the 5' end and identical to primer P2 at the 3' end.

Primer P1 is labeled with a fluorescent, radioactive or other suitable marker. Thus, when the sense and antisense strands are separated, the sense strand will be labeled.

Primer P2 is a reverse primer for the STR locus. Primer P2 will be modified by adding a certain number (X) of nucleotides to form a long P2 primer, or deleting a certain number (Y) nucleotides to form a short P2 primer. The number of nucleotides added or deleted would preferably be the same. In addition, it is most preferred to add or delete the number of nucleotides contained in the repeat unit of the STR locus, such that the bracketing markers produced would be a fixed repeat number of nucleotides shorter or longer in length than the STR region.

As shown in FIG. 3, the short P2 primer would be hybridized to the shortest allele, and the long P2 primer would be hybridized to the longest allele. Using the short allele and long allele as templates, extension products from the short P2 primer and long P2 primer, each combined with the labeled P1 forward primer, are amplified. As can be seen in FIG. 3 the extension product with the short P2 primer lacks portion Y which would be present with unmodified primer P2, and the extension product with the long P2 primer includes portion X which would not be present with the unmodified primer P2. The extension products would therefore have a known number of nucleotides greater or less than the PCR product created with unmodified primers P1 and P2, and these products would closely bracket the PCR product created with the unmodified primers P1 and P2.

Because the length of the bracketing markers will be accurately known (from addition X and subtraction Y), and they will have a mobility during electrophoresis similar to the PCR allelic products created with unmodified primers P1 and P2, and because they will not overlap with the known or common allelic region of the genetic locus, these bracketing, locus compatible markers will enable the length of the STR locus to be accurately determined.

Figure 4:
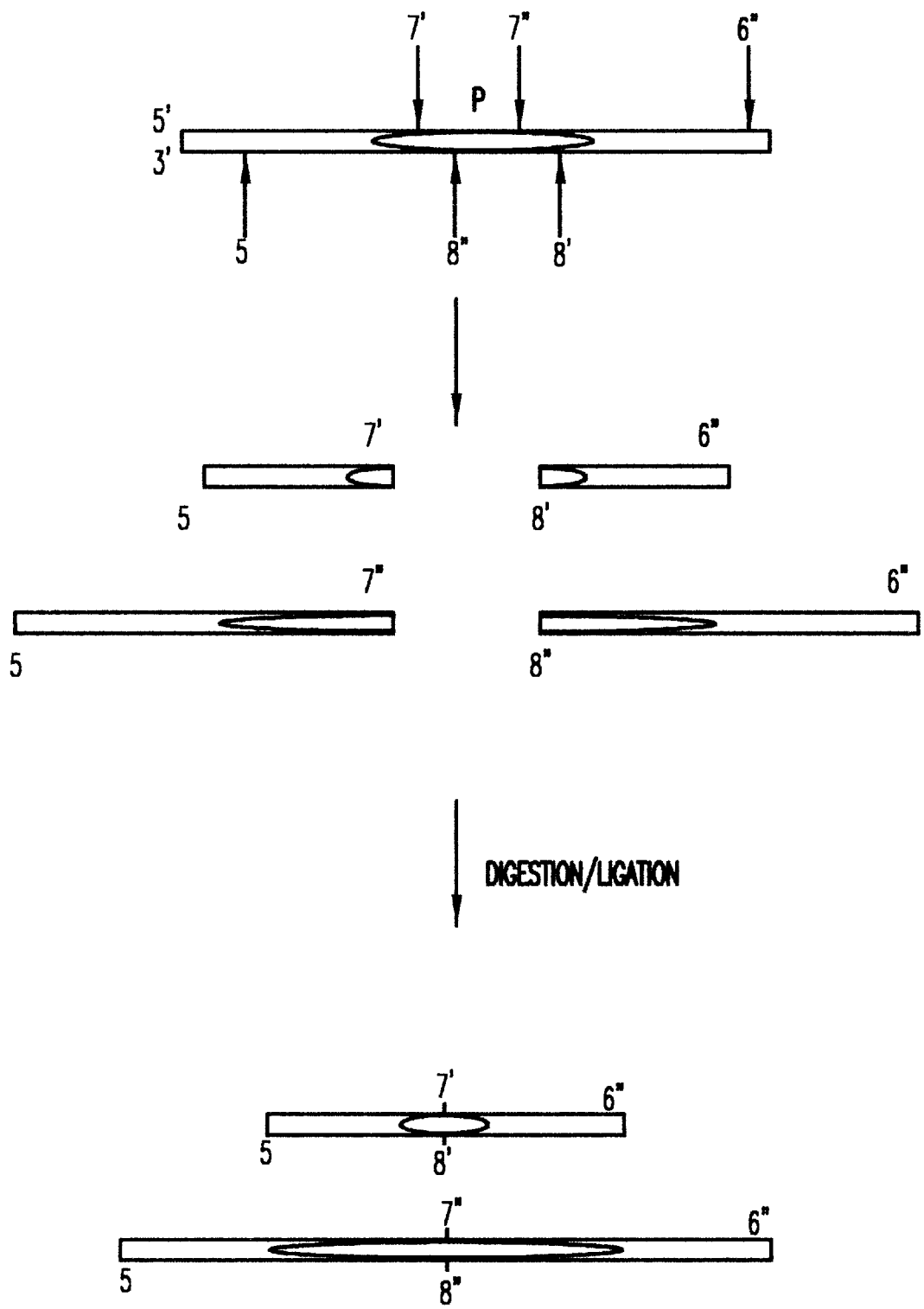
FIG. 4 is a schematic drawing showing yet another strategy used in the practice of this invention.

FIG. 4 shows the design for deleting and inserting repeat units in the polymorphic region itself rather than in unique flanking sequences in order to create variant alleles shorter or longer than any naturally occurring allele or common allele. The classical PCR product amplified from genomic DNA by a pair of classical STR primers, forward primer 5 and reverse primer 6", is divided into two portions from the repeat region. The 5' portion of the classical product is amplified by the classical forward primer 5 paired with reverse primers 7' and 7", respectively, from the repeat region. The reverse primer 7' contains half of the repeat units of the short variant allele. The reverse primer 7" contains half of the repeat units necessary to create the long variant allele. The 3' portion of the classical product is amplified by the classical reverse primer 6" paired with forward primers 8' and 8", respectively, from the repeat region. The forward primer 8' contains the half of repeat units for creating the short allele. The forward primer 8" contains the other half of the repeat units for creating the long allele. Each of the four primers from the repeat region starts with extra nt at its 5' end, which is recognized by a seamless restriction enzyme, such as for example Eam 1104 I, continues with repeat unit nts, and ends with flanking sequence nt at its 3' end. After PCR, each of the four fragments is digested by a seamless restriction enzyme (e.g., Eam 1104 I) and ligated by T4 DNA ligase into two fragments. The fragment amplified by primer pair 7' and 5 is ligated with the fragment amplified by primer pair 8' and 6" to form the short allele or shortest common allele. The fragment amplified by primer pair 7" and 5 is ligated with fragment amplified by primer pair 8" and 6" to form the long allele or longest common allele. Upon electrophoretic separation, the shortest and longest common alleles would bracket the naturally occurring or "common" allele; thereby enabling accurate length determinations to be made.

EXAMPLES

The following examples are presented to illustrate the advantages of the present invention and to assist one of ordinary skill in the art in making and using the same. However, the examples should not be interpreted to limit the scope of the invention disclosed and set forth in the appended claims.

Example 1

Creation of Locus Compatible Bracketing Markers for Measurement of the Polymorphic CDR3 Region Lengths of V7 Family Genes From the TCRA Locus During lymphopoiesis, each TCRA gene is assembled through somatic recombination from among one each of over 50 AV segment genes, 63 AJ segment genes, and a single AC segment gene (see, Davis et al., Nature 334.394–402,1988; and Moss et al., Eur. J. Immunol. 23:1153–1159, 1993). The length and sequence polymorphic CDR3 region between the AV and AC segments is created from the variable portion of the AJ segment by nucleotide deletion and N nucleotide addition. The range of TCRA CDR3 region lengths is 0–17aa (Liu, D., Dau, P., U.S. patent application Ser. No. 08/559,205, which is herein incorporated by reference). Based on sequence homology, TCRA genes are grouped into 32 families whose polymorphic CDR3 regions are amplified by family specific AV segment forward primers in combination with a common AC segment reverse primer. These gene segments thereby serve as flanking sequences for the CDR3 fragment length polymorphism of each particular TCRAV gene family.

Since a common AC segment primer is employed to hybridize with the downstream flanking sequence in amplification of the CDR3 fragment length polymorphisms of all TCRAV families, two additional AC segment primers were created to hybridize with AC sequences located 5' and 3' from the classical AC segment primer binding site in order to amplify short and long DNA fragments to bracket the classically amplified fragments upon electrophoresis.

The principle of this method is applicable to all AV families because the identical downstream flanking AC segment primer is employed for amplification of the polymorphic CDR3 region in conjunction with different AV upstream flanking primers specific for each family. However, newly designed AC primers must be thermally and sequence compatible with each of the family specific AV primers with which they are paired. Because of the homogenous PCR templates employed, thermal compatibility is less of a factor, enabling the same newly designed AC segment primers discussed below to successfully be paired with all 28 AV segment primers barring sequence incompatibility between any pair. Incompatible primer pairs can be redesigned to hybridize with different AV or AC specific sequences until a compatible pair is found for each AV family.

cDNA from T cell clone No. 263 was amplified in separate PCR reactions, each employing a forward primer specific for one of twenty nine TCRAV families (Genevée et al., Eur. J. Immonol. 22:1261–1269, 1993) in conjunction with a common AC 129 reverse primer amplifying the first 129 nt of the flanking AC segment's 5' end. T cell clones yielded a specific product from only one reaction. Non-specific products were excluded by fragment length determination upon sequencing gel electrophoresis or by sequencing. cDNA amplified with the AV7-AC 129 primer pair was found to be monoclonal, have a CDR3 region length of 27 nt, express the AJ26 gene segment of nt, and to have a total fragment length of 349 nt. Additionally, a molecular clone (No. 147) was derived from molecular cloning of AV7-AC 129 amplified polyclonal cDNA derived from PBMC. Cloning of blunt ended PCR products was carried out with the pCR-Script SK(+) cloning kit (Stratagene, La Jolla, Calif.). Upon sequencing, M147 had a CDR3 length of 30 nt, expressed the AJ5 gene segment, and had a fragment length of 352 nt.

Because the classical AC segment reverse primer amplifies the 5' 57 nt of the AC segment, short and long reverse AC segment primers were designed which amplified the 5' 27 and 87 nt of the AC segment, respectively, yielding products 30 nt shorter or longer than the classical product. Thus, with clone No. 147 DNA as template, these bracketing markers would encompass a CDR3 region of 0 to 60 nt, thereby encompassing the expected CDR3 length range of sample TCRA DNA.

Figure 5A:
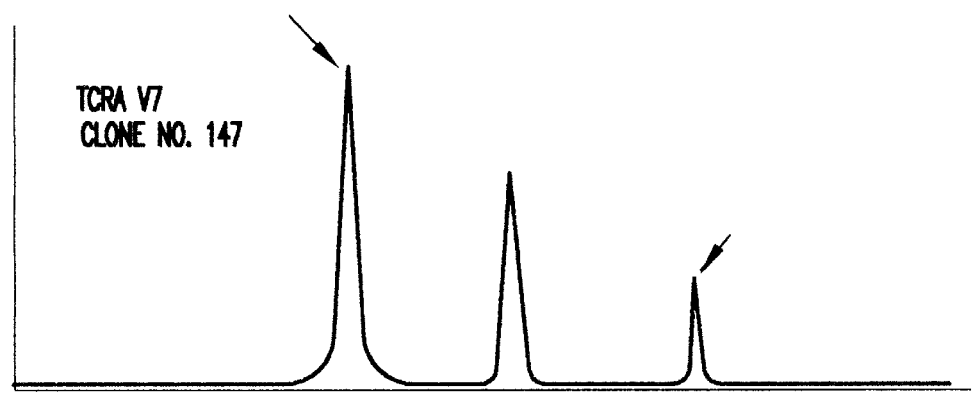
FIGS. 5a–b are computerized Fragment Manager™ scans of polyacrylamide electrophoresis gel lanes pertaining to Example 1 showing locus compatible bracketing markers for the polymorphic CDR3 region of the TCRAV7 gene.
Figure 5B:
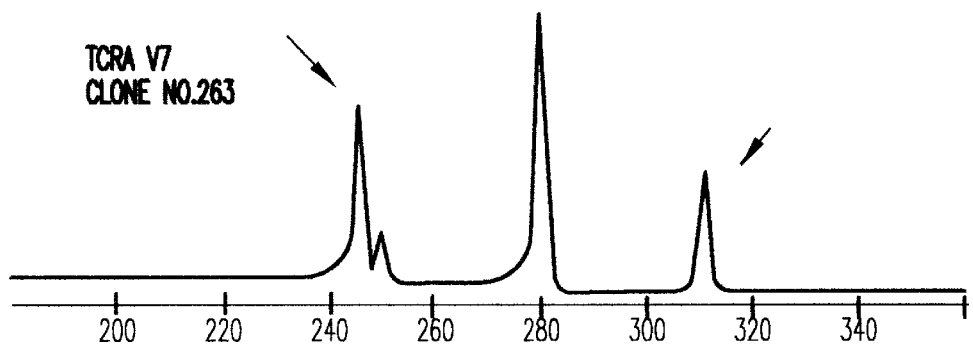

All three TCRAC segment primers were 5' labeled with Cy5 for fluorescence detection. FIGS. 5a–b show that when the 3 AC segment primers were combined with the AV7 segment primers in separate PCR reactions, these AC primers yielded PCR products 60 nt apart. FIG. 5a shows that clone No. 147 has corresponding fragment lengths of 250, 280, and 310 bp. FIG. 5b shows that clone no. 263 has fragments 247, 277, and 307 in length correlating with its 3 nt shorter CDR3 region.

DNA from these clones plus PCR amplified AV7 family specific DNA from an additional 15 clones which had been sequenced and amplified with the AV7/AC57 primer pair were measured by electrophoretic fragment analysis using the locus indifferent 100/350 bp and 200/350 bp markers and the CA27 and CA87 locus compatible markers, described above, as bracketing standards. The results were compared to their lengths determined by sequencing. When the 247–307 bp bracketing marker pairs were employed on the A.L.F. Express, the greatest deviation measured was 0.3 nt (mean 0.10±0.13 nt), which is well within the desired value of less than 1.5 nt. For the 250/310 bp bracketing marker pair, the deviation was higher at 0.6 nt (mean 0.25±0.15 nt), reflecting CDR3 region sequence heterogeneity between the two pairs of AV7 family specific bracketing markers. A far greater deviation (4.25±0.23 nt) from the true fragment length was found with the 100/350 bp locus indifferent markers. The mean deviation was reduced to 1.08±0.11 nt when the 200/350 bp indifferent standard markers were employed, showing the effects of sequence heterogeneity between the 100 and 200 bp standard markers and tightness of bracketing standards relative to sample DNA.

Example 2

Creation of Locus Compatible Bracketing Markers for Measurement of the Polymorphic CDR3 Region Length of V16 Family Genes from the TCRB Locus During lymphopoiesis each TCRB gene is assembled through somatic recombination from among each of 45 TRCBV segment genes, 2 BD segment genes, 13 BJ segment genes, and 2 BC segment genes (see, Davis et al., Nature 334:395–402 (1988); Rowen et al. Science 272:1755–1762 (1996)). The length and sequence polymorphic CDR3 region lies between the BV and BC segments, and is created from the BD and variable portion of the BJ segments by nt deletion and N nt addition. Based on sequence homology, TCRB genes are grouped into 25 families or subfamilies, whose polymorphic CDR3 regions are amplified by different family specific BV forward primers in combination with a common BC segment reverse primer. The gene segments thereby serve as flanking sequences for the CDR3 polymorphism of each particular TCRBV gene family.

In order to bracket the common BC segment primer, two additional BC segment primers were created to hybridize with BC sequences located 5' and 3' from the classical BC segment primers in order to amplify shorter and longer DNA fragments in combination with BV family specific primers. The amplified DNA fragment lengths bracketed the classically amplified fragments upon electrophoresis. In principle, this technology is applicable to any BV family because their identical or highly similar BC segments allow a common 3' flanking BC primer to be employed for amplification of the polymorphic CDR3 region of all BV genes in conjunction with their 5' flanking family specific BV primers. However, newly designed BC primers must be thermally and sequence compatible with each of the family specific BV primers with which they are paired. Thermal incompatibility is less important because of the highly purified PCR templates, which enable the same newly designed BC segment primers discussed below to be paired with all 25 BV segment family specific primers baring sequence incompatibility between any pair. Incompatible primer pairs can be redesigned to hybridize with different BV or BC specific sequences until a compatible pair is found for each BV family.

cDNA for T cell clone No. 296 served as template for 25 separate PCR reactions. Each employed a forward primer specific for one of 25 TCRBV families (see, Liu et al., *J. Immunol. Meth.* 187:139–1 50 (1995)) in conjunction with a common BC 54 reverse primer which amplified the first 54 nt of the flanking BC segment's 5' end. The T cell clone yielded a specific product with only the BV16 family specific primer. Non-specific amplification products were excluded by determining if the product was in the appropriate length range for that BV family upon automated polyacrylamide sequencing gel electrophoresis or of appropriate sequence by DNA cycle sequencing on the same instrument.

cDNA amplified with BV16-BC168 primer pair was monoclonal with a length of 363 bp as determined by its sequence. Its CDR3 region was 30 nt, and it employed the BJ1.2 gene segment. Because the classical BC segment reverse primer amplifies 54 nt of the BC segment's 5' end, a short reverse primer amplifying the 5' 24 nt of the BC segment and a long reverse primer amplifying the 5' 92 nt of this BC segment were designed. One set of the three BC segment primers was produced labeled with fluorescein, and another labeled with Cy5.

The family specific BV16 primer combined with the classical BC54 reverse primer generated a TCR specific fragment encompassing the 3' terminal region of the V segment, the entire CDR3 region, the entire J region, and the 5' terminal end of the C gene segment to position 54. The sequence of this fragment was 249 bp. Additional DNA fragments were generated by repeating the PCR reaction with either the BC24 or BC92 primers in place of the CB54 primer. In this way TCRBV16 specific fragments of 219 and 287 bp were generated of identical locus specific sequence to the 249 bp fragment except for the length of their BC segment 3' extension.

Figure 6:
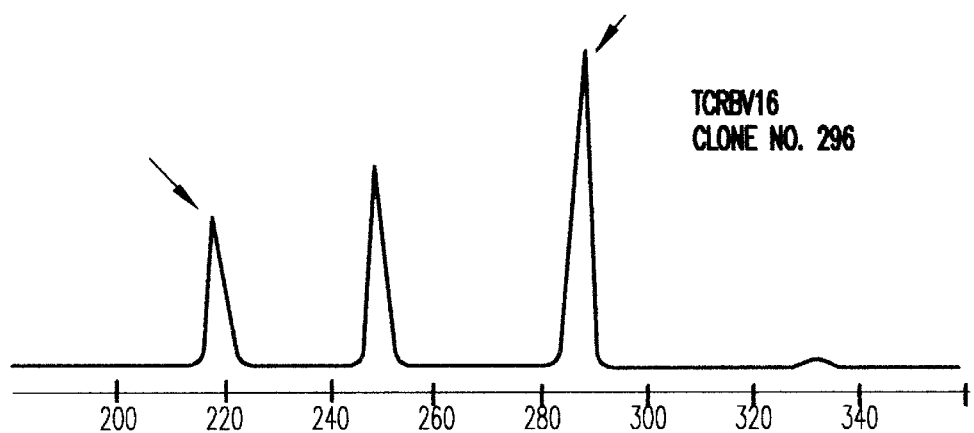
FIG. 6 is a Fragment Manager™ scan of a polyacrylamide electrophoresis gel lane pertaining to Example 2 showing locus compatible bracketing markers for the polymorphic CDR3 Region of the TCR BV16 gene.

FIG. 6 shows the separation of the 219 and 287 bp locus specific products bracketing the classical 249 bp product. When electrophoresed on the A.L.F. instrument the 249 bp fragment registered a deviation of −0.3 nt measured with these locus compatible markers. The 100/300 bp locus indifferent standards co-electrophoresed in the same lane were unable to identify the 249 bp product reliably, measuring it with a deviation of −1.5 nt. Twelve additional BV16 specific T cell clones were identified and these TCR3 CDR3 regions were measured together with that of clone No. 296. The mean absolute deviation registered with the 219/287 bp locus specific bracketing pair was 0.52±0.38 nt. The range of deviation was −0.3 to +0.8 nt, reflecting in part sequence incompatibility between the CDR3 regions and J segments of the bracketing locus compatible markers with the individual clones, as well as their differing BC segment lengths. Measured with the 100/300 bp bracketing indifferent standard pair co-electrophoresed in the same lanes the mean absolute deviation was 0.81±0.49 nt.

To access the impact of a different running condition, chiefly increased temperature, on these results, this experiment was repeated on the A.L.F. Express. Then the absolute measured deviation lessened to 0.17±0.21 nt employing the locus compatible bracketing standards, but it increased to 3.31±0.74 nt with the locus indifferent standards co-electrophoresed in the same lanes. This result demonstrates the relative resistance of locus compatible standards compared to indifferent standards to change in deviation with altered running conditions. The greater sequence and length incompatibility between the locus indifferent standards and locus specific DNA allows different running conditions to increase their disparate mobility, which in turn produces greater measurement error. The gel polymers, electrophoretic running buffers and length of migration pathway were identical between the A.L.F. and A.L.F. Express instruments.

Overall, these results demonstrate improvement in the amount of deviation to be more reliably within the necessary value of less than 1.5 nt when electrophoretic measurement of a TCR gene fragment is carried out with bracketing locus compatible internal lane standards as compared to bracketing locus indifferent internal standards. These differences in measurement error become critical when TCR fragment lengths are determined by electrophoresis because they differ in length by multiples of 3 nt due to amino acid additions or deletions in their CDR3 regions. Therefore, polymorphic CDR3 fragments can only be reliably discriminated from each other if the error is less than 1.5 nt.

Example 3

Creation of Locus Compatible Bracketing Markers for the STR Loci CSF1PO, FESFPS, and F13A01 by Modification of Flanking Sequences Locus compatible bracketing markers for three STR loci were created by adding or deleting nucleotides at the end of long or short alleles from each locus. In order to create bracketing markers with electrophoretic mobilities similar to the STR molecules being measured four nucleotides were added to one end of the longest allele or deleted from the shortest allele available in the Promega allelic ladder through the following procedure:

First, three allelic ladders from the Promega Corp., CSF1PO, FESFPS and F13A01 were cloned into plasmid vectors and transformed into bacteria in order to isolate the shortest and the longest alleles present in each ladder (PCR-Script amp SK(+) Cloning Kit, Stratagene).

Second, two reverse primers were designed for each of the three STR loci. These reverse primers are shown in Table 1, and were made by either deleting 4 nt of genomic sequence or adding 4 nt of repeat or genomic DNA sequence at the 5' end of the original primer sequence.

Third, the forward primer was labeled with fluorescein at its 5' end without any sequence change based on the published primer sequences (see Table 1).

Fourth, the isolated shortest alleles from each of the three loci were used as templates in PCR with their own shortened reverse primer paired with their fluorescein labeled forward primer. The longest alleles were amplified by their own lengthened reverse primers paired with their fluorescein labeled forward primer.

Figure 7A:
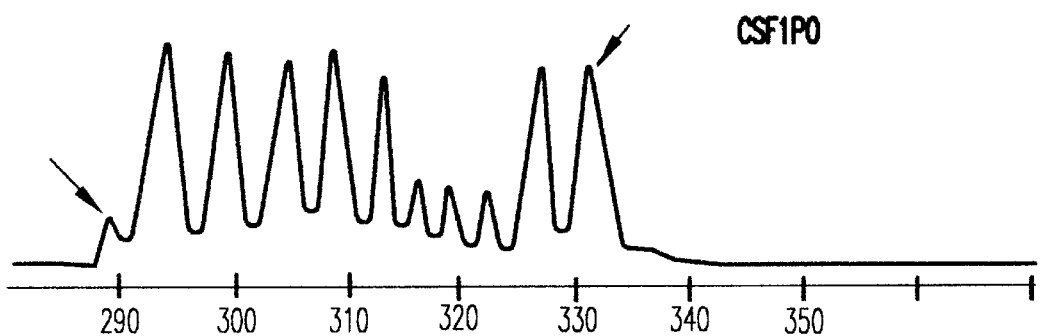
FIGS. 7a–c are Fragment Manager™ scans of lanes of a polyacrylamide electrophoresis gel pertaining to Example 3 showing locus compatible bracketing markers for the STR Loci CSF1OPO, FESFPS, and F13A01 by modification of flanking sequences.
Figure 7B:
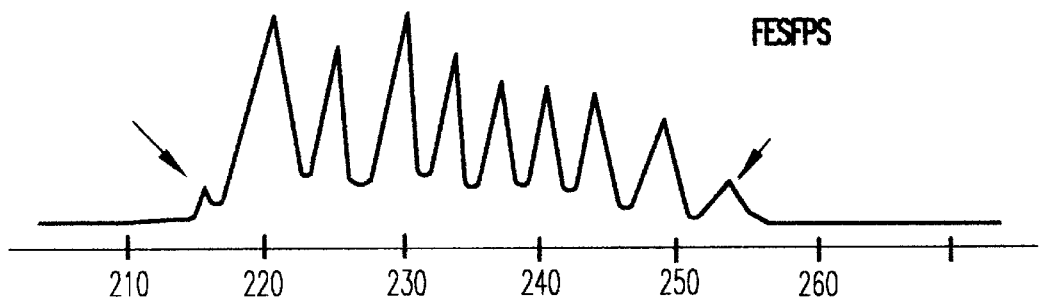
Figure 7C:
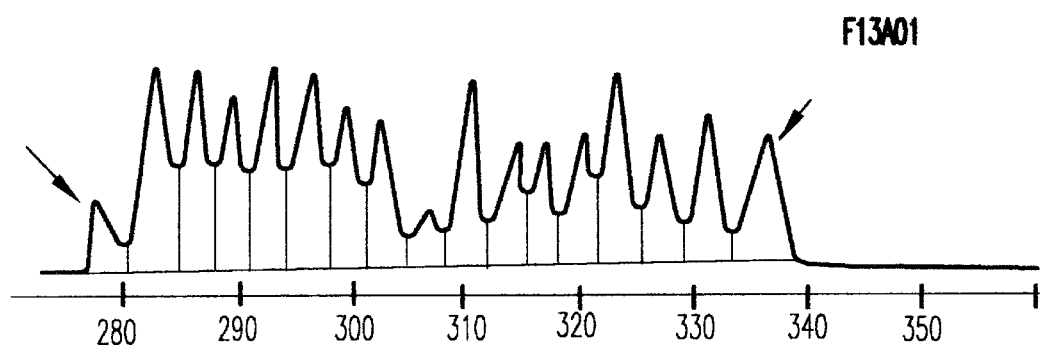

The bracketing markers created for each locus were loaded into the same lane of a polyacrylamide gel as their locus specific allelic ladder and subjected to electrophoresis with the A.L.F. automated DNA sequencer. FIGS. 7a–c show that the locus compatible bracketing markers for the STR Loci CSF1PO, FESFPS, and F13A01 tightly bracket their alleles of origin.

Example 4

Validation of Locus Compatible Bracketing STR Markers in Calibration of Electrophoretic Mobility The locus compatible bracketing STR Markers were co-electrophoresed as internal or external and internal standards to calibrate the electrophoretic measurement of the alleles of their loci and compared to the use of standard locus indifferent bracketing markers and the shortest and longest true alleles of allelic ladders from each locus as markers. For each data point the determinations were made for all three STR loci run in at least three scattered lanes of each of five polyacrylamide sequencing gels. The different sets of external or internal markers to be compared were always co-electrophoresed in the same gel lanes. The absolute deviation of each measurement from the expected value was then calculated. Results are presented in Table 2.

CALIBRATION

| Locus | external (ext.) Stand. Ladder | external (ext.) allelic ladder | internal (int.) Stand. Bracketing | internal (int.) Locus comp. Bracketing | internal (int.) allelic bracketing | Ext. plus int. Stand. Latter plus Stand. Bracketing | Ext. plus int. allelic ladder and locus com patible bracketing |
|---|---|---|---|---|---|---|---|
| CSF1P0 | 2.9 ± 0.15* | 1.90 ± 0.13 | 0.63 ± 0.05 | 0.32 ± 0.07 | 0.08 ± 0.04 | 0.94 ± 0.06 | 0.01 ± 0.02 |
| FESFPS | 2.37 ± 2.02 | 2.36 ± 2.59 | 1.18 ± 0.16 | 0.16 ± 0.18 | 0.04 ± 0.06 | 1.24 ± 0.16 | 0.04 ± 0.06 |
| F13A01 | 2.02 ± 2.38 | 2.89 ± 3.33 | 1.85 ± 0.71 | 0.17 ± 0.21 | 0.11 ± 0.14 | 1.87 ± 0.69 | 0.10 ± 0.12 |

*Mean ± SD (nt)

External standard markers composed of either a locus indifferent standard ladder or an allelic ladder were equally inferior. They could not reliably discriminate between the alleles of any of the three loci because discrimination of the tetrameric tandem repeat alleles requires a measurement error of less than two nt.

Standard locus indifferent markers performed better when applied as internal bracketing standards, but for all three STR loci taken together they produced a deviation 5.6 fold higher than locus compatible bracketing standards. Short and long true alleles produced less deviation than modified alleles when employed as bracketing standards because their sequences were more compatible with the measured alleles than the manufactured locus compatible bracketing standards.

Standard locus indifferent external ladders combined with standard locus indifferent internal bracketing markers produced no improvement in deviation over the standard locus indifferent internal bracketing markers by themselves. Allelic external standards plus external bracketing locus compatible markers corrected the deviation associated with internal bracketing locus compatible markers down to the level of internal alleles as bracketing markers.

The locus compatible bracketing standards were then used to measure the length of sample DNA alleles derived from seven individuals of two nuclear families and the K562 control sample. The measured deviations were almost identical to the values obtained for the STR allelic ladders shown in Table 2: CSF1PO 0.28±0.12; FESFPS 0.26±0.15; and F13A01 0.22±0.18 nt.

Internal locus compatible bracketing standards showed low Standard Deviations in measurement of true alleles. This finding signifies that because their mobility is highly similar to the alleles from which they are derived, under different lane to lane and gel to gel running conditions their mobility shifts in register with the alleles they are measuring, thereby keeping the measured deviation relatively constant.

Example 5

Use of Run Time to Measure DNA Fragment Length

The run times (RTs) of short (sb) and long (lb) bracketing locus compatible or specific markers and bracketed unknown (u) sample alleles can be used to calculate the unknown (u) fragment lengths. Equations 1 and 2 are employed to calculate the length (L) of all unknown (u) sample alleles of the CSF1PO, FESFPS, and F13A01 loci from their RTs on the A.L.F. instrument. The sb and lb markers for each locus were created under the condition of subtraction or addition of 4 nt of genomic DNA sequence to the flanking reverse PCR primers of each locus.

$$\text{Rate (min/nt)} = RT_{lb} - RT_{sb} / L_{lb} - L_{sb} \qquad \text{EQ 1}$$

$$Lu = RTu - RT_{sb} / \text{Rate} + L_{sb} \qquad \text{EQ 2}$$

The calculated average deviations and SDs of the measured fragment lengths for each locus are small as follows: CSF1PO 0.09±0.07 nt, FESFPS 0.18±0.18 nt, and F13A01 0.17±0.20 nt.

There is very little difference in the low mean allelic deviation between the A.L.F. and A.L.F. Express systems measured by bracketing F13A01 derived locus compatible standards and calculation of fragment length by either Fragment Manager™ software (0.16 and 0.14 nt) or RTs (0.16 and 0.12 nt). However, when locus indifferent standard markers are used the mean deviation between the two systems becomes higher with both devices, and is more than twice as great with the A.L.F. as with the A.L.F. Express (1.25 and 0.60 nt, 1.25 and 0.60 nt).

This observation again shows the resistance to change of the relative mobilities of locus compatible standards and sample alleles subjected to different operating conditions. The usefulness of RTs in making these calculations will allow them to be used by appropriately designed computer software to identify sample alleles. In other electrophoresis systems which compare band migration distance over a fixed time rather than using RTs, the migration distance can also be calibrated by locus compatible or specific markers in a manner analogous to the use of RTs through the use of an appropriately designed computer program.

Example 6

Creation of Locus Specific Bracketing Markers Through Modification of the Number of Tandem Repeat Units Within STR Polymorphic Regions to be Amplified and Their Validation as Bracketing Standard Markers for Electrophoresis Calibration Adding or deleting tandem repeat units in the polymorphic (repeat) region of an STR allele can be used to create variant alleles for use as bracketing markers which are more "locus specific" than locus compatible markers created by adding or deleting nt at either the 3' or 5' end of an allelic DNA fragment. In case of a non-unitary repeat sequence, addition or deletion of the core repeat unit would usually be undertaken. Locus F13A01, with an allelic range of 4–16 repeat units including a 3.2 allele due to a shortened flanking sequence, is used as an example to explain how these markers are created.

First, two reverse primers (short and long) and two forward primers (short and long) are designed from the repeat region (Table 1, F13A01 rev 251-Eam-1, F13A01 rev 275-Eam-9, F13A01 fwd 268-Eam-2, and F13A01 fwd 248-Eam-9). Each primer incorporates 6 nt at its 5' end which can be recognized by restriction enzyme Eam 1104, followed by the desired number of repeat nts and ending with a specific flanking sequence at its 3' end.

Second, the 2 reverse primers from the repeat region are each paired with the classical F13A01 forward primer in separate PCR, respectively, to amplify the cloned long allele in step 1 of Example 3 or any allele from locus F13A01 containing an adequate number of repeat units for primer hybridization. Each of the 2 forward primers from the repeat region is paired with the classical F13A01 reverse primer in separate PCR, respectively, to amplify the same cloned long allele or any allele from the F13A01 locus containing an adequate number of repeat units for primer hybridization.

Third, each PCR product from the second step is digested with Eam 1104 (Stratagene) and electrophoresed on a 2% NuSieve (FMC Bioproducts) mini-gel. The digested PCR product with the desired length is retrieved from the NuSieve gel and purified with QIAEX II (Qiagen Inc., Chatsworth, Calif.).

Fourth, the two digested short PCR products made from the F13A01 rev 251-Eam-1 reverse primer paired with forward primer F13A01 fwd 190 and F13A01 fwd 268-Eam-2 forward primer paired with reverse primer F13A01 rev. 484 are ligated by T4 DNA ligase according to the manufacturer's instructions (Boehringer Mannheim) to form the short locus specific bracketing marker with 2 repeat units. The two digested long PCR products from F13A01 rev 275-Eam-9 reverse primer paired with forward primer F13A01 fws 190 and F13A01 fwd 248-Eam-9 forward primer paired with reverse primer F13A01 rev. 484 are ligated by T4 DNA ligase to form the long locus specific bracketing marker with 17 repeat units. Both ligation products are verified by sequencing.

Fifth, the short and long locus specific bracketing markers are amplified by locus specific primers and cloned directly into plasmid DNA with a PCR-Script amp (SK+) cloning kit (Stratagene) for replication.

There are several other known mutagenesis technologies which might be useful in creating locus specific variant alleles, and they will be well known to investigators in the field.

Manufactured variant alleles would preferentially differ in DNA sequence from their neighbor alleles only by the presence or absence of 1–2 repeat units, thus giving them the same relationship to their neighbor allele as true alleles to each other. In different situations, for example, the presence of non-integer alleles, the repeat number of variant alleles might preferentially differ from their nearest neighbor allele by fractional or multiple repeat units. The RT of each true allele can then be used for identification by means of variant alleles as calibrating markers because its length as a fraction of the bracketed polymorphic region will be proportional to the fraction of its RT interval from the short marker divided by the total run time interval from the short to long variant allele.

Another significant advantage of the manufactured variant allelic bracketing markers is the amplification of their template DNA by PCR primer kits designed to amplify polymorphic genomic loci by binding to the same flanking regions. Because variant allelic markers incorporate the same or longer flanking sequences as true alleles into their templates, they are co-amplified by the locus specific primers used in PCR to amplify the unknown genomic DNA alleles from that locus.

The co-amplified markers and sample DNA are loaded together into the same lane for electrophoresis. Marker and sample DNA are readily detected because they share the same differential label and migrate without overlap. Not only do the bracketing markers accurately measure the unknown DNA fragment length, but also play a role of positive control for the PCR step in sample analysis.

Figure 8A:
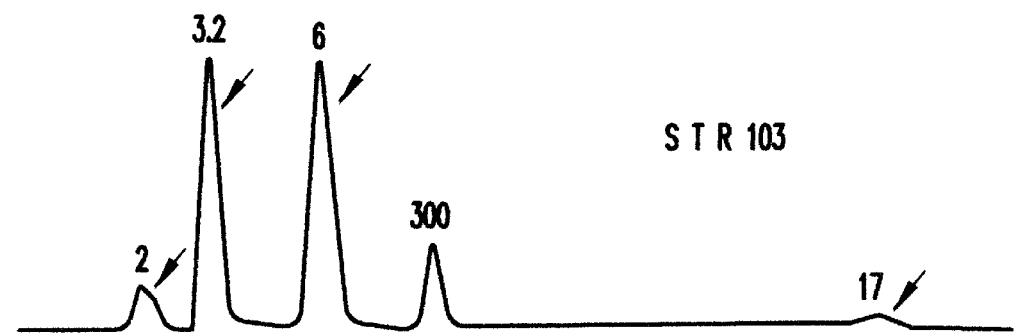
FIGS. 8a–c are Fragment Manager™ scans of lanes of a polyacrylamide electrophoresis gel pertaining to Example 6 showing locus specific bracketing markers for the STR locus F13A01 created by decreasing or increasing the number of tandem repeat units within the polymorphic region and the effect on DNA fragment peaks of the differential addition of an extra nucleotide by Taq DNA polymerase.
Figure 8B:
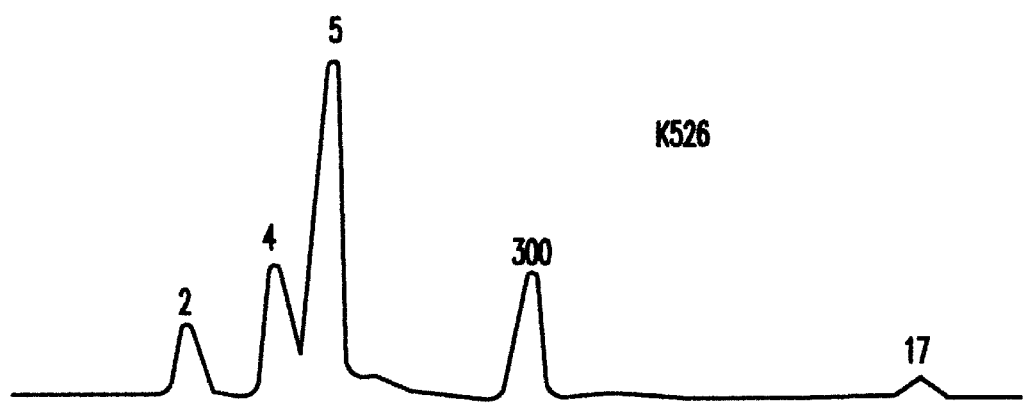
Figure 8C:
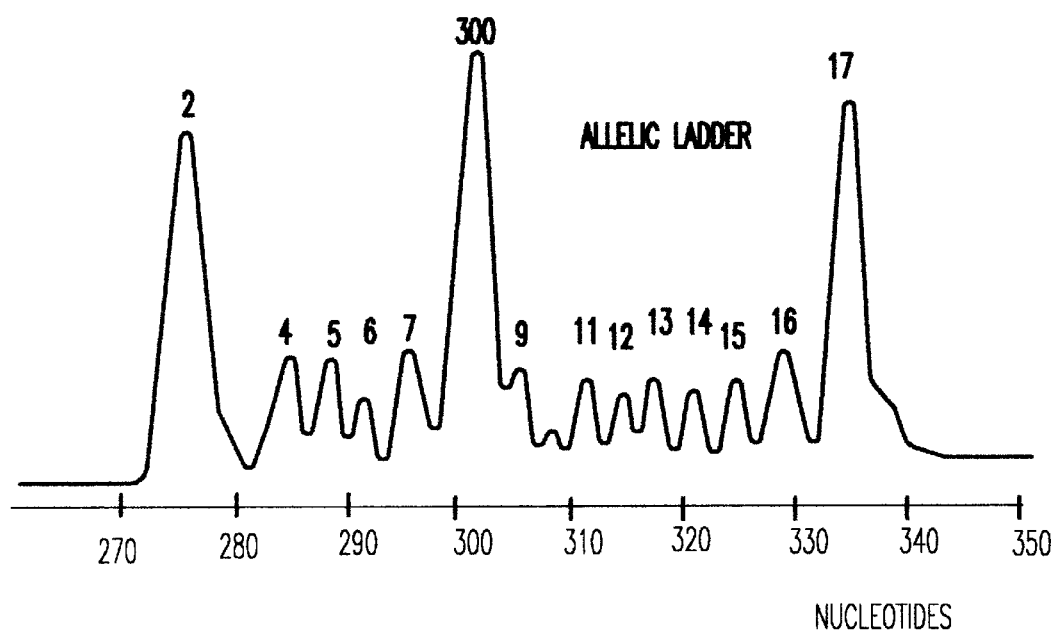

FIGS. 8a–c shows electrophoretic scans of F13A01 specific short and long bracketing markers which are co-amplified in the same PCR tube, with genomic DNA sample STR103 (8a), control DNA K562 (8b), and the F13A01 allelic ladder (8c), respectively. Three non-locus compatible standard markers (250, 300 and 350 nt) were loaded into each lane for comparison. The short and long variant alleles and the true alleles are designated by their allelic number based on the number of repeat units in each allele. The 300 nt standard marker obscures allele 8 in FIG. 8c by overlapping it. Each group of PCR products is electrophoresed on 3 different lanes. The average variance and standard deviation measured by bracketing standard markers (250/350, Pharmacia) and the bracketing locus specific markers (275/335, short and long) are 1.32±0.39 nt vs −0.20±0.05 nt for alleles 3.2 and 6 from the sample DNA, −1.17±0.40 nt vs −0.05±0.07 nt for alleles 4 and 5 from control DNA K562, and −0.47±0.31 nt vs −0.02±0.08 nt for all alleles of the allelic ladder.

Another advantage of the co-amplification of the locus specific bracketing markers and the sample DNA in the same PCR tube is that PCR products from both the bracketing markers and sample DNA will have the same proportion with an extra nucleotide added to their 3' end by Taq DNA polymerase. Addition of an extra nucleotide by Taq DNA polymerase to a proportion of the sample DNA to be measured is a source of measurement error if a different proportion of the calibrating standard DNA receives an extra nucleotide in a different PCR amplification, or the calibrating standard DNA is not a PCR product or is a non-Taq related PCR product. Furthermore, under the co-amplification conditions, Taq DNA polymerase appears to generate fewer non-specific products, including stutter peaks, from genomic DNA.

Figure 9:
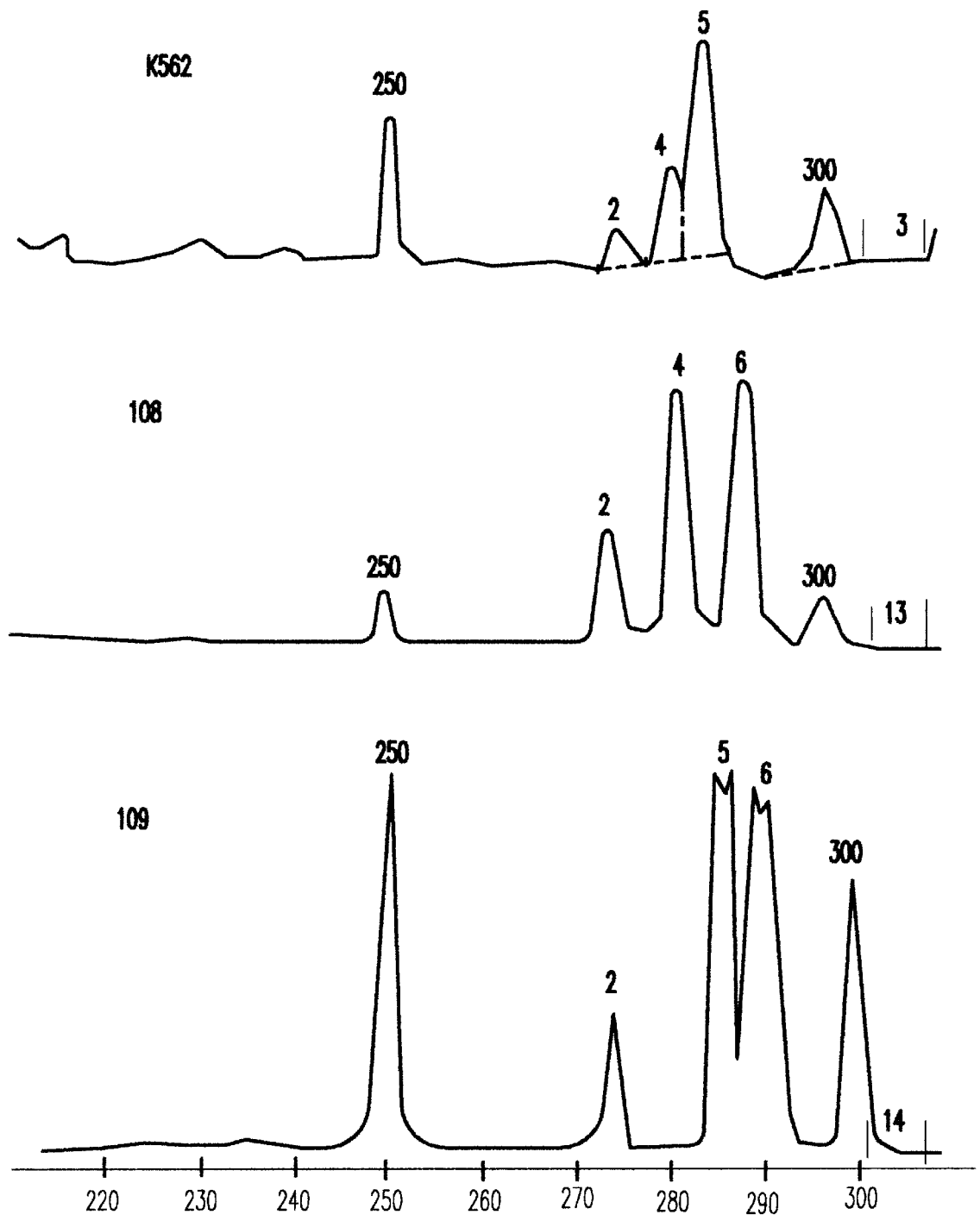
FIG. 9 is a Fragment Manager™ scan of lanes of a polyacrylamide electrophoresis gel pertaining to Example 6 showing the effect of extra nucleotide addition by Taq DNA polymerase on the DNA fragment peaks visualized after their PCR co-amplification of the F13A01 locus from three different genomic DNA samples, each together with the short variant allele bracketing marker.

FIG. 9 shows that the standard DNA markers of 200 and 300 nt in each lane have symmetrical peaks without apparent extra nucleotide addition. The short variant allele and two true alleles amplified with F13A01 locus specific primers from genomic DNA sample K562 show a rightward peak shift due to extra nucleotide addition to a majority of the fragments. The short variant allele and two true alleles amplified from genomic DNA sample 108 show extra nucleotide addition to a minority of fragments which is not enough to shift the peaks. The short variant allele and two true alleles amplified from genomic sample 109 show biphasic peaks due to addition of an extra nucleotide to about one-half of their DNA fragments by Taq DNA polymerase.

The bracketing locus specific markers can be extended into the flanking region beyond the classical primer pair binding sites to produce extended templates for PCR in case of the need for modification of the classical primer pair for any reason. For example, instead of pairing with one of the classical primer pair, the reverse primer F13A01 rev 251-Eam-1 from the repeat region pairs with forward primer F13A01 fwd 1 (Table 1), which yields an extra 189 nt upstream from the classical forward primer upon PCR amplification. Similarly, the forward primer F13A01 fwd 248 Eam-2 from the repeat region pairs with the reverse primer F13A01 rev 628 (Table 1), which yields an extra 146 nt downstream from the classical reverse primer.

FIG. 10 shows the 260 bp (lane 2) PCR product from primer pair of fwd 1 and Eam-1 and the 369 bp (lane 3) PCR product from Eam-2 and rev 628 primer pair. After being digested by Eam 1104, the 2 DNA fragments were joined together by T4 DNA ligase and re-amplified by the classical primer pair. Lane 4 of FIG. 10 shows the amplified 275 bp short bracketing marker from the extended template. All sample DNA products shown in FIG. 10 have been verified by sequencing. Therefore, the extended, ligated DNA fragment (F13A01 fwd 1-rev 628) can be used as a template for co-amplification with an unknown DNA sample by any primer pair designed within its 5' and 3' flanking sequence.

Kits for PCR or mPCR co-amplification and co-electrophoresis of locus compatible bracketing markers, locus specific STR markers, and locus specific variant alleles may include any or all of the following: 1) DNA templates for short and long locus specific bracketing markers for each locus to be measured, 2) PCR primer pairs binding to specific 5' and 3' flanking sequences for each locus, 3) deoxyribose nucleotide triphosphates (dNTPs) and buffers appropriate for PCR, 4) a thermostable DNA polymerase appropriate for PCR, and 5) instructions and reagents for sample DNA extraction and quantitation to ensure that the amount of sample DNA is compatible with the pre-dispensed template DNAs. Typical reagents used to extract genemoic DNA from whole blood include $NH_4Cl$, potassium acetate, Rnase A, isopropanol, ethanol, EDTA, SDS, and NaOH. Computer software can be designed to measure DNA sample fragment lengths by means of calibration with bracketing locus compatible or specific markers. Co-amplification and co-electrophoresis in PCR and mPCR of locus compatible bracketing markers or locus specific STR markers with sample DNA containing unknown alleles of a locus may used for the purpose of identification (genotyping), and will be particularly powerful when performed with 2–20 genetic loci.

While the invention has been described in terms of its preferred embodiments, those skilled in the art will recognize that the invention can be practiced with modification within the spirit and scope of the appended claims.

We claim:

1. Primer sets which produce locus compatible markers for determining DNA fragment lengths of a polymorphic region, comprising:
   primary forward and primary reverse primers which respectively hybridize to upstream and downstream sequences which flank a polymorphic region of a DNA sample, at least one of said primary forward and primary reverse primers including a first detectable label, said primary forward primer hybridizing to an antisense strand of DNA of said DNA sample, said primary reverse primer hybridizing to a sense strand of DNA of said DNA sample, said primary forward and primary reverse primers encompassing a first section in said DNA sample which includes said polymorphic region; and
   first and second secondary reverse primers which hybridize to said sense strand of DNA at first and second locations, respectively, each of which are downstream of said polymorphic region, said first location located within said first section of said DNA sample, the 3' end of said second location located downstream of said first section.

2. The primer sets of claim 1 further comprising second and third detectable labels respectively on said first and second secondary reverse primers.

3. The primer sets of claim 1 wherein said first and second secondary reverse primers are a selected number of nucleotides shorter and longer, respectively, than said primary reverse primer.

4. The primer sets of claim 1 wherein said polymorphic region of said DNA sample includes short tandem repeat sequences of nucleotides.

5. The primer sets of claim 1 wherein said polymorphic region of said DNA sample is a CDR3 region.

6. Primer sets for a DNA polymorphic region containing short tandem repeat (STR) sequences, comprising:
   primary forward and primary reverse primers which respectively hybridize to upstream and downstream flanking sequences of said DNA polymorphic region, said primary forward primer hybridizing to an antisense strand of said upstream flanking sequence, and said primary reverse primer hybridizing to a sense strand of said downstream flanking sequence;
   two secondary reverse primers which hybridize to said sense strand of said DNA;
   two secondary forward primers which hybridize to an antisense strand of said DNA, said two secondary reverse primers and said two secondary forward primers hybridizing to oligonucleotide sequences between said primary forward and said primary reverse primers, and wherein at least one of the following parameters exists:
   (A) a first of said two secondary reverse primers overlaps a second of said two secondary reverse primers by a first known sequence of nucleotides, and
   (B) a first of said two secondary forward primers overlaps a second of said two secondary forward primers by a second known sequence of nucleotides.

7. The primer sets of claim 6 wherein each of said two secondary reverse primers includes a restriction site.

8. The primer sets of claim 6 wherein each of said two secondary forward primers includes a restriction site.

9. The primer sets of claim 6 further comprising a detectable label associated with at least one primer selected from the group consisting of said primary forward primer, said primary reverse primer, said two secondary reverse primers, and said two secondary forward primers.

10. A method for determining DNA fragment lengths of a polymorphic region of a genetic locus, comprising the steps of:

preparing first and second secondary reverse primers which hybridize with a sense strand of DNA at first and second locations both of which are downstream of said polymorphic region of a genetic locus;

amplifying by polymerase chain reaction short and long locus compatible bracketing markers for alleles of said polymorphic region using in combination said first and second secondary reverse primers and primary forward and primary reverse primers which respectively hybridize to upstream and downstream flanking sequences of said polymorphic region, said primary forward primer hybridizing to an anti-sense strand of DNA, said primary reverse primer hybridizing to said sense strand of DNA, said primary forward and primary reverse primers encompassing a first section in said DNA which includes said polymorphic region, said first secondary reverse primer hybridizing within said first section and the 5' end of said second secondary reverse primer hybridizing downstream of said first section; and detecting short and long locus compatible markers for each allele.

11. The method of claim 10 wherein said detecting step includes the steps of separating said short and long locus compatible bracketing markers, and determining run times for said short and long locus compatible bracketing markers.

12. The method of claim 10 wherein said detecting step includes the step of separating said short and long locus compatible bracketing markers by electrophoresis.

13. The method of claim 10 further comprising the step of labeling said first and second secondary reverse primers.

14. A method for determining DNA fragment lengths of alleles in a polymorphic region, comprising the steps of:

preparing two secondary reverse primers which hybridize to a sense strand of DNA and two secondary forward primers which hybridize to an antisense strand of DNA, said two secondary reverse primers and said two secondary forward primers hybridizing to oligonucleotide sequences between a primary forward and a primary reverse primer;

amplifying by polymerase chain reaction PCR products from said polymorphic region using said two secondary reverse primers in combination with said primary forward primer which hybridizes with an upstream flanking sequence of said polymorphic region and said two secondary forward primers in combination with said primary reverse primer which hybridizes with the downstream flanking sequence of said polymorphic region, said amplifying step producing four PCR products, a first of said PCR products having on one end a first of said two secondary reverse primers and on another end said primary forward primer, a second of said PCR products having on one end a first of said secondary forward primers and on another end said primary reverse primer, a third of said PCR products having on one end a second of said two secondary reverse primers and on another end said primary forward primer, and a fourth of said PCR products having on one end a second of said two secondary forward primers and on another end said primary reverse primer;

combining by ligation two of said PCR products to form a short variant allelic marker;

combining by ligation the remaining two of said PCR products to form a long variant allelic marker; and detecting said short and long variant allelic markers.

15. The method of claim 14 wherein said two combining steps are performed by ligation.

16. The method of claim 14 wherein said detecting step includes the steps of separating said short and long variant allelic markers, and determining run times for said short and long variant allelic markers.

17. The method of claim 14 wherein said detecting step includes the step of separating said short and long variant allelic markers by electrophoresis.

18. The method of claim 14 further comprising the step of labeling said short and long variant allelic markers.

19. Locus specific markers produced by the process of:

carrying out a polymerase chain reaction (PCR) using primary forward and primary reverse primers which hybridize to upstream and downstream flanking sequences of a polymorphic region of a DNA sample, said primary forward primer hybridizing to an antisense strand of DNA of said DNA sample, said primary reverse primer hybridizing to a sense strand of DNA of said DNA sample, and two secondary reverse primers which hybridize to a sense strand of DNA in said DNA sample and two secondary forward primers which hybridize to an antisense strand of DNA in said DNA sample wherein both said two secondary reverse primers and said two secondary forward primers hybridize to nucleotides between said primary forward and primary reverse primers, to produce four DNA products;

combining by ligation two of said DNA products to make a short variant allelic marker; and combining by ligation the remaining two of said DNA products to make a long variant allelic marker.

20. Locus compatible markers produced by the process of:

carrying out a polymerase chain reaction using primary forward and primary reverse primers which respectively hybridize to upstream and downstream flanking sequences of a polymorphic region of a DNA sample, at least one of said primary forward and primary reverse primers including a first detectable label, said primary forward primer hybridizing to an antisense strand of DNA of said DNA sample, said primary reverse primer hybridizing to a sense strand of DNA of said DNA sample, said primary forward and primary reverse primers encompassing a first section in said DNA sample which includes said polymorphic region, and first and second secondary reverse primers which respectively hybridize to said sense strand of DNA at first and second locations each of which are downstream of said polymorphic region, said first location located within said first section of said DNA sample, and the 3' end of said second location located downstream of said first section; and obtaining short and long locus compatible bracketing markers from said polymerase chain reaction step which are respectively shorter and longer than said first section.

21. A method of preparing locus compatible markers for a polymorphic region, comprising the steps of:

cloning an allelic ladder into a plasmid vector, said allelic ladder being created from primary forward and primary reverse primers for a genomic sequence;

transforming the plasmid vector into a host;

isolating a short and a long allele in said allelic ladder;

labeling a primary forward primer to produce a labeled primary forward primer;

preparing short and long secondary reverse primers by, respectively, deleting a first known number of nucleotides from said primary reverse primer, and by adding a second known number of nucleotides to said primary reverse primer;

using said short allele as a template in PCR with said labeled primary forward primer and said short secondary reverse primer; and using said long allele as a template in PCR with said labeled primary forward primer and said long secondary reverse primer.

22. A method of producing locus specific markers comprising the steps of:

carrying out a polymerase chain reaction with primary forward and primary reverse primers which hybridize to upstream and downstream flanking sequences of a polymorphic region of a DNA sample, said primary forward primer hybridizing to an antisense strand of DNA of said DNA sample, said primary reverse primer hybridizing to a sense strand of DNA of said DNA sample, and two secondary reverse primers which hybridize to a sense strand of DNA in said DNA sample and two secondary forward primers which hybridize to an antisense strand of DNA in said DNA sample wherein both said two secondary reverse primers and said two secondary forward primers hybridize to nucleotides between said primary forward and primary reverse primer hybridization sites, to produce four DNA products;

combining by ligation two of said DNA products to make a short variant allelic marker; and combining by ligation the remaining two of said DNA products to make a long variant allelic marker.

23. The method of claim 22 wherein each of said two combining steps is performed by ligation.

24. The method of claim 22 wherein said polymorphic region includes a short tandem repeat sequence.

25. The method of claim 24 wherein said two reverse primers include first and second oligonucleotide sequences which hybridize to said sense strand of DNA at a common region where a first of said two secondary reverse primers overlaps a second of said two secondary reverse primers by a multiple of a repeat unit of said STR sequence.

26. The method of claim 25 wherein said multiple is an integer of at least one.

27. The method of claim 22 wherein each of said two secondary reverse primers includes a restriction site.

28. The method of claim 24 wherein said two secondary forward primers include first and second nucleotide sequences which hybridize to said antisense strand of DNA at a common region where a first of said two secondary forward primers overlaps a second of said two secondary forward primers by a multiple of a repeat unit of said STR sequence.

29. The method of claim 28 wherein said multiple is an integer of at least one.

30. The method of claim 22 wherein each of said two secondary forward primers includes a restriction site.

31. The method of claim 24 wherein said two secondary forward primers include first and second oligonucleotide sequences which hybridize to said antisense strand of DNA at a first common region where a first of said two secondary forward primers overlaps a second of said two secondary forward primers by a first multiple of a repeat unit of said STR sequence, and wherein said two secondary reverse primers include third and fourth oligonucleotide sequences which hybridize to said sense strand of DNA at a second common region where a first of said two secondary reverse primers overlaps a second of said two secondary reverse primers by a second multiple of said repeat unit of said STR sequence.

32. The primer sets of claim 31 wherein said first and second multiples are equivalent.

33. The primer sets of claim 31 wherein said first and second multiples are not equivalent.

34. A method of producing locus compatible markers comprising the steps of:

carrying out a polymerase chain reaction using primary forward and primary reverse primers which respectively hybridize to upstream and downstream flanking sequences of a polymorphic region of a DNA sample, at least one of said primary forward and primary reverse primers including a first detectable label, said primary forward primer hybridizing to an antisense strand of DNA of said DNA sample, said primary reverse primer hybridizing to a sense strand of DNA of said DNA sample, said primary forward and primary reverse primers encompassing a first section in said DNA sample which includes said polymorphic region, and first and second secondary reverse primers which respectively hybridize to said sense strand of DNA at first and second locations each of which are downstream of said polymorphic region, said first location located within said first section of said DNA sample, and the 3' end of said second location located downstream of said first section; and obtaining short and long locus compatible bracketing markers from said polymerase chain reaction step which are respectively shorter and longer than said first section.

35. The method of claim 34 further comprising the step of adding second and third detectable labels respectively to said first and second secondary reverse primers.

36. The method of claim 34 wherein said first and second secondary primers are a selected number of nucleotides shorter and longer, respectively, than said primary reverse primer.

37. The method of claim 34 wherein said polymorphic region of said DNA sample includes short tandem repeat sequences of nucleotides.

38. The method of claim 34 wherein said polymorphic region of said DNA sample is a CDR3 region.

39. Primer sets which produce locus compatible markers for determining DNA fragment lengths of a polymorphic region of a genetic locus, comprising:

primary forward and reverse primers which respectively hybridize to upstream and downstream flanking sequences which flank a polymorphic region of a genetic locus of a DNA sample, at least one of said primary forward and reverse primers including a first detectable label, said primary forward primer hybridizing to an antisense strand of DNA of said DNA sample, said primary reverse primer hybridizing to a sense strand of DNA of said DNA sample, said primary forward and primary reverse primers flanking a first section in said DNA sample which includes said polymorphic region; and first and second secondary forward primers which hybridize to said antisense strand of DNA at first and second locations, respectively, each of which are upstream of said polymorphic region, said first location located within said first section of said DNA sample, said second location located upstream of said first section.

40. The primer sets of claim 39 further comprising second and third detectable labels respectively on said first and second secondary forward primers.

41. The primer sets of claim 39 wherein said first and second secondary forward primers are a selected number of nucleotides shorter and longer, respectively, than said primary reverse primer.

42. The primer sets of claim 39 wherein said polymorphic region of said DNA sample is a CDR3 region.

43. A method for determining DNA fragment lengths of a polymorphic region of a genetic locus, comprising the steps of:

preparing first and second secondary forward primers which hybridize with an anti-sense strand of DNA at first and second locations both of which are upstream of a polymorphic region of a genetic locus;

amplifying by polymerase chain reaction short and long locus compatible bracketing markers for alleles of said polymorphic region using in combination said first and second secondary forward primers and primary forward and primary reverse primers which respectively hybridize to upstream and downstream flanking sequence of said polymorphic region, said primary forward primer hybridizing to an anti-sense strand of DNA, said primary reverse primer hybridizing to a sense strand of DNA, said primary forward and primary reverse primers flanking a first section in said DNA which includes said polymorphic region, said first secondary forward primer hybridizing at a location located within said first section and said second secondary forward primer hybridizing a location located upstream of said first section; and detecting short and long locus compatible markers for each allele.

44. Locus compatible markers produced by the process of:

carrying out a polymerase chain reaction using primary forward and primary reverse primers which respectively hybridize to upstream and downstream flanking sequences of a polymorphic region of a DNA sample, at least one of said primary forward and primary reverse primers including a first detectable label, said primary forward primer hybridizing to an antisense strand of DNA of said DNA sample, said primary reverse primer hybridizing to a sense strand of DNA of said DNA sample, said primary forward and primary reverse primers encompassing a first section in said DNA sample which includes said polymorphic region, and first and second secondary forward primers which respectively hybridize to said antisense strand of DNA at first and second locations each of which are upstream of said polymorphic region, said first location located within said first section of said DNA sample, and the 3' end of said second location located upstream of said first section; and obtaining short and long locus compatible bracketing markers from said polymerase chain reaction step which are shorter and longer than said first section.

45. A method of producing locus compatible markers comprising the steps of:

carrying out a polymerase chain reaction using primary forward and primary reverse primers which respectively hybridize to upstream and downstream flanking sequences of a polymorphic region of a DNA sample, at least one of said primary forward and primary reverse primers including a first detectable label, said primary forward primer hybridizing to an antisense strand of DNA of said DNA sample, said primary reverse primer hybridizing to a sense strand of DNA of said DNA sample, said primary forward and primary reverse primers encompassing a first section in said DNA sample which includes said polymorphic region, and first and second secondary forward primers which respectively hybridize to said antisense strand of DNA at first and second locations each of which are upstream of said polymorphic region, said first location located within said first section of said DNA sample, and the 3' end of said second location located upstream of said first section; and obtaining short and long locus compatible bracketing markers from said polymerase chain reaction step which are shorter and longer than said first section.

46. The method of claim 14 wherein said polymorphic region includes a short tandem repeat sequence.

47. The markers of claim 19 wherein said polymorphic region includes a short tandem repeat sequence.

48. The method of claim 21 wherein said polymorphic region includes a short tandem repeat sequence.

49. A method for determining DNA fragment lengths of alleles in a polymorphic region comprising the steps of:

cloning an allelic ladder into a plasmid vector, said allelic ladder being created from primary forward and primary reverse primers for a genomic sequence;

transforming the plasmid vector into a host;

isolating a short and a long allele in said allelic ladder;

labeling a primary forward primer to produce a labeled primary forward primer;

preparing short and long secondary reverse primers by, respectively, deleting a first known number of nucleotides from said primary reverse primer, and by adding a second known number of nucleotides to said primary reverse primer;

using said short allele as a template in PCR with said labeled primary forward primer and said short secondary reverse primer; and using said long allele as a template in PCR with said labeled primary forward primer and said long secondary reverse primer; and detecting short and long locus compatible markers for each allele.

50. The method of claim 49 wherein said polymorphic region includes a short tandem repeat sequence.

51. The primer sets of claim 6 wherein both parameters A and B exist.

52. A method for calculating the length of a DNA fragment of unknown length for a genetic locus, comprising the steps of measuring the electrophoretic run time in minutes of a short and a long bracketing marker for said genetic locus, calculating a rate of minutes per nucleotide for said short and long bracketing markers using an Equation 1: Rate (minutes/nucleotide)=$Rt_{lb}-Rt_{sb}/Rt_{lb}-Rt_{sb}/L_{lb}-L_{sb}$, wherein $RT_{lb}$ is the electrophoretic run time in minutes of said long bracketing marker, $RT_{sb}$ is the electrophoretic run time in minutes of said short bracketing marker, $L_{lb}$ is the length in nucleotides of said long bracketing marker, and $L_{sb}$ is the length in nucleotides of said short bracketing marker, and determining the length of said DNA fragment of unknown length using an Equation 2: $L_u = RT_u - RT_{sb}/Rate + L_{sb}$, wherein $L_u$ is the length of the DNA fragment of unknown length, $RT_u$ is the electrophoretic run time in minutes of said DNA fragment of unknown length, $RT_{sb}$ is the electrophoretic run time in minutes of said short bracketing marker, $L_{sb}$ is the length in nucleotides of said short bracketing marker, and Rate is said rate of minutes per nucleotide calculated using said Equation 1 in said calculating step.

53. The method of claim 52 wherein said long and short bracketing markers are locus specific bracketing markers.

54. The method of claim 52 wherein said long and short bracketing markers are locus compatible bracketing markers.

55. A process of co-amplification, comprising the step of:
co-amplifying by polymerase chain reaction locus specific bracketing markers of claim 19 for a genetic locus with alleles of said genetic locus.

56. A process of co-amplification, comprising the step of:
co-amplifying by polymerase chain reaction locus compatible markers of claim 20 for a genetic locus with alleles of said genetic locus.

57. A process of co-amplification, comprising the step of:
co-amplifying by polymerase chain reaction locus compatible markers of claim 44 for a genetic locus with alleles of said genetic locus.

\* \* \* \* \*

SEQUENCE LISTING

<160> NUMBER OF SEQ ID NOS: 28

<210> SEQ ID NO 1

-continued

```
<211> LENGTH: 24
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 1
gcaacatgct ggcggagcac ccac                                              24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 2
cacggcaggg tcagggttct g                                                 21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 3
gtcactggat ttagagtct                                                    19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 4
atcaaaatcg gtgaataggc ag                                                22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 5
atacacatca gaatccttac tttg                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 6
aaagagtcta aacaggatga gtcc                                              24

<210> SEQ ID NO 7
<211> LENGTH: 18
<212> TYPE: DNA
```

```
<213> ORGANISM: Artificial Sequence
<220> FEATURE:
<223> OTHER INFORMATION: Description of Artificial Sequence:PRIMER
                        SEQUENCE

<400> SEQUENCE: 7
tgggaacacg tttttcag                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 8
ttctgatggc tcaaacac                                                 18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 9
cttttgggtg tgggagatct c                                             21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 10
cacaccagtg tggccttttg                                               20

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 11
tcgtcgaccc cactgtgcac ctccttccc                                     29

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 12
aacctgagtc tgccaaggac tagc                                          24

<210> SEQ ID NO 13
<211> LENGTH: 20
<212> TYPE: DNA
<213> ORGANISM: Artificial Sequence
<220> FEATURE:
```

-continued

<223> OTHER INFORMATION: Description of Artificial Sequence:PRIMER
                SEQUENCE

<400> SEQUENCE: 13
acacaccact ggccatcttc                                           20

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:PRIMER
                SEQUENCE

<400> SEQUENCE: 14
atctttccac acaccactgg ccatcttc                                  28

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:PRIMER
                SEQUENCE

<400> SEQUENCE: 15
aatcccaaca ctttgggaag c                                         21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:PRIMER
                SEQUENCE

<400> SEQUENCE: 16
gaggttgcac tccagccttt gcaa                                      24

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:PRIMER
                SEQUENCE

<400> SEQUENCE: 17
atctcttcaa agaaagagta aaagaaaaaa att                            33

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence:PRIMER SEQUENCE

<400> SEQUENCE: 18
atctcttcaa agaaagaaag aaagaaagaa agaaagaaag aaagagt             47

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:PRIMER
                SEQUENCE

<400> SEQUENCE: 19
atctcttcac tttcatcttt ctatctttca gatg                     34

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 20
atctcttcac tttctttctt tctttctttc tttctttctt tctttcat      48

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 21
tgaatcatcc cagagccaca                                     20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 22
ttcctgaatc atcccagagc caca                                24

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 23 cttttcctg aatcatccca gagccaca                             28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 24
tgcattcctg aatcatccca gagccaca                            28

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:PRIMER
      SEQUENCE

<400> SEQUENCE: 25

-continued

```
atgctttttgc ctggcaggtc agc                                          23

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 26
gcttgttaat tcatgtaggg aaggc                                         25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 27
tcccagctac ttggctactc                                               20

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:PRIMER
                        SEQUENCE

<400> SEQUENCE: 28
atttgtagtc ccagctactt ggctactc                                      28
```